US009018440B2

(12) United States Patent
Yu et al.

(10) Patent No.: US 9,018,440 B2
(45) Date of Patent: Apr. 28, 2015

(54) FLUORESCENT MOUSE MODEL

(75) Inventors: Congrong (Ron) Yu, Leawood, KS (US); Limei Ma, Leawood, KS (US)

(73) Assignee: Stowers Institute for Medical Research, Kansas City, MO (US)

( * ) Notice: Subject to any disclaimer, the term of this patent is extended or adjusted under 35 U.S.C. 154(b) by 614 days.

(21) Appl. No.: 12/312,094

(22) PCT Filed: Oct. 24, 2007

(86) PCT No.: PCT/US2007/022611
§ 371 (c)(1),
(2), (4) Date: Feb. 16, 2010

(87) PCT Pub. No.: WO2008/153543
PCT Pub. Date: Dec. 18, 2008

(65) Prior Publication Data
US 2010/0154068 A1 Jun. 17, 2010

Related U.S. Application Data

(60) Provisional application No. 60/863,301, filed on Oct. 27, 2006.

(51) Int. Cl.
*A01K 67/00* (2006.01)
*G01N 33/00* (2006.01)
*A01K 67/027* (2006.01)

(52) U.S. Cl.
CPC ....... *A01K 67/0275* (2013.01); *A01K 2217/052* (2013.01); *A01K 2217/203* (2013.01); *A01K 2227/105* (2013.01); *A01K 2267/0393* (2013.01); *C12N 2830/003* (2013.01)

(58) Field of Classification Search
USPC ....................................................... 800/18, 3
See application file for complete search history.

(56) References Cited

U.S. PATENT DOCUMENTS

| 4,736,866 | A | | 4/1988 | Leder et al. |
| 4,870,009 | A | | 9/1989 | Evans et al. |
| 4,873,191 | A | | 10/1989 | Wagner et al. |
| 4,873,316 | A | | 10/1989 | Meade et al. |
| 5,824,837 | A | * | 10/1998 | Chen et al. ........................ 800/3 |
| 2002/0165364 | A1 | | 11/2002 | Tsien et al. |
| 2005/0019261 | A1 | | 1/2005 | Albrecht et al. |

OTHER PUBLICATIONS

Halsey. Stroke 21:1573-1578, 1990.*
Naito et al. J Reprod Fert 113:137-143, 1998.*
Bai et al., "Regulation of kidney-specific Ksp-cadherin gene promoter by hepatocyte nuclear factor-1β," Am. J. Physiol. Renal Physiol., vol. 283, pp. F839-F851 (2002).
Baird et al., "Circular permutation and receptor insertion within green fluorescent proteins," Proc. Natl. Acad. Sci USA, vol. 96, pp. 11241-11246 (1999).
Banerji et al., "A Lymphocyte-Specific Cellular Enhancer Is Located Downstream of the Joining Region in Immunoglobulin Heavy Chain Genes," Cell, vol. 33, pp. 729-740 (1983).
Berrettini et al., "Quantitative trait loci mapping of three loci controlling morphine preference using inbred mouse strains," Nature Genetics, vol. 7, pp. 54-58 (1994).
Bozza et al., "In Vivo Imaging of Neuronal Activity Neurotechnique by Targeted Expression of a Genetically Encoded Probe in the Mouse," Neuron, vol. 42, pp. 9-21 (2004).
Bullard et al., "Cutting-Edge Technology IV. Genomic engineering for studies of the gastrointestinal tract in mice," Am. J. Physiol. Gastrointest. Liver Physiol., vol. 283, pp. G1232-G1237 (2002).
Byrne et al., "Multiplex gene regulation: A two-tiered approach to transgene regulation in transgenic mice," Proc. Natl. Acad. Sci. USA, vol. 86, pp. 5473-5477 (1989).
Calame et al., "Transcriptional Controlling Elements in the Immunoglobulin and T Cell Receptor Loci," Advances in Immunology, vol. 43, pp. 235-275 (1988).
Camper et al., "Postnatal repression of the α-fetoprotein gene is enhancer independent," Genes & Development, vol. 3, pp. 537-546 (1989).
Crabbe et al., "Genetic Animal Models of Alcohol and Drug Abuse," Science, vol. 264, pp. 1715-1723 (1994).
De Sanctis et al., "Quantitative locus analysis of airway hyperresponsiveness in A/J and C57BL/6J mice," Nature Genetics, vol. 11, pp. 150-154 (1995).
Diez-Garcia et al., "Activation of cerebellar parallel fibers monitored in transgenic mice expressing a fluorescent Ca2+ indicator protein," European Journal of Neuroscience, vol. 22, pp. 627-635 (2005).
Edlund et al., "Cell-Specific Expression of the Rat Insulin Gene: Evidence for Role of Two Distinct 5' Flanking Elements," Science, vol. 230, pp. 912-916 (1985).
Feinbaum, "Vectors Derived From Plasmids—Introduction to Plasmid Biology," Current Protocols in Molecular Biology, Section II, Unit 1.5, pp. 1.5.1-1.5.17 (1998).
Frankel et al., "Genetic Epilepsy Model Derived From Common Inbred Mouse Strains," Genetics, vol. 138, pp. 481-489 (1994).
Früh et al., "Displacement of housekeeping proteasome subunits by MHC-encoded LMPs: a newly discovered mechanism for modulating the multicatalytic proteinase complex," The EMBO Journal, vol. 13, No. 14, pp. 3236-3244 (1994).
Furth et al., "Temporal control of gene expression in transgenic mice by a tetracycline-responsive promoter," Proc. Natl. Acad. Sci. USA, vol. 91, pp. 9302-9306 (1994).
Fussenegger, "The Impact of Mammalian Gene Regulation Concepts on Functional Genomic Research, Metabolic Engineering, and Advanced Gene Therapies," Biotechnol. Prog., vol. 17, pp. 1-51 (2001).

(Continued)

*Primary Examiner* — Marcia S Noble
(74) *Attorney, Agent, or Firm* — Bryan Cave LLP

(57) ABSTRACT

The present invention relates to compositions and methods useful for detecting and/or measuring, e.g., intracellular signaling in vivo. More particularly, compositions and methods are provided, which include transgenic animals, that are useful in mapping and examining, e.g., calcium fluctuations in vivo between and within populations of cells in real time. Methods for screening for candidate compounds that effect, e.g., intracellular calcium signaling are also provided.

11 Claims, 14 Drawing Sheets

(56) References Cited

OTHER PUBLICATIONS

Go et al., "Optimization and direct comparison of the dimerizer and reverse tet transcriptional control systems," J. Gene Med., vol. 4, pp. 258-270 (2002).

Hasan et al., "Functional Fluorescent Ca2+ Indicator Proteins in Transgenic Mice under TET Control," PLoS Biology, vol. 2, No. 6, pp. 0763-0775 (2004).

Hasty et al., "Aging and Genome Maintenance: Lessons from the Mouse?" Science, vol. 299, pp. 1355-1359 (2003).

Hyman et al., "Quantitative Trait Locus Analysis of Susceptibility to Diet-Induced Atherosclerosis in Recombinant Inbred Mice," Biochemical Genetics, vol. 32, Nos. 11/12, pp. 397-407 (1994).

Kellendonk et al., "Inducible Site-specific Recombination in the Brain," J. Mol. Biol., vol. 285, pp. 175-182 (1999).

Kessel et al., "Murine Developmental Control Genes," Science, vol. 249, pp. 374-379 (1990).

Kistner et al., "Doxycycline-mediated quantitative and tissue-specific control of gene expression in transgenic mice," Proc. Natl. Acad. Sci. USA, vol. 93, pp. 10933-10938 (1996).

Kühn et al., "Inducible Gene Targeting in Mice," Science, vol. 269, pp. 1427-1429 (1995).

Metzger et al., "Transgenic mice expressing a pH and Cl-sensing yellow-fluorescent protein under the control of a potassium channel promoter," European Journal of Neuroscience, vol. 15, pp. 40-50 (2002).

Pinkert et al., "An albumin enhancer located 10 kb upstream functions along with its promoter to direct efficient, liver-specific expression in transgenic mice," Genes & Development, vol. 1, pp. 268-276 (1987).

Queen et al., "Immunoglobulin Gene Transcription is Activated by Downstream Sequence Elements," Cell, vol. 33, pp. 741-748 (1983).

Rubera et al., "Specific Cre/Lox Recombination in the Mouse Proximal Tubule," J. Am. Soc. Nephrol., vol. 15, pp. 2050-2056 (2004).

Tallini et al., "Imaging cellular signals in the heart in vivo: Cardiac expression of the high-signal Ca2+ indicator GCaMP2," PNAS, vol. 103, No. 12, pp. 4753-4758 (2006).

West et al., "Dietary Obesity Linked to Genetic Loci on Chromosomes 9 and 15 in a Polygenic Mouse Model," J. Clin. Invest., vol. 94, pp. 1410-1416 (1994).

Wimmel et al., "Inducible acceleration of G1 progression through tetracycline-regulated expression of human cyclin E," Oncogene, vol. 9, pp. 995-997 (1994).

Winoto et al., "A novel, inducible and T cell-specific enhancer located at the 3' end of the T cell receptor α locus," The EMBO Journal, vol. 8, No. 3, pp. 729-733 (1989).

* cited by examiner

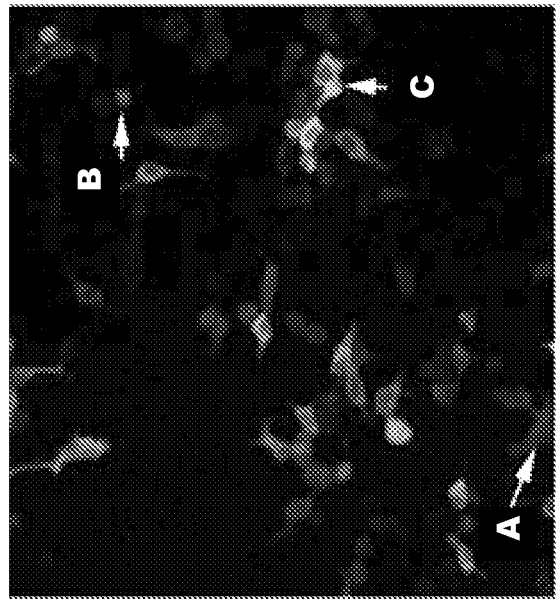
FIG. 1A  Control
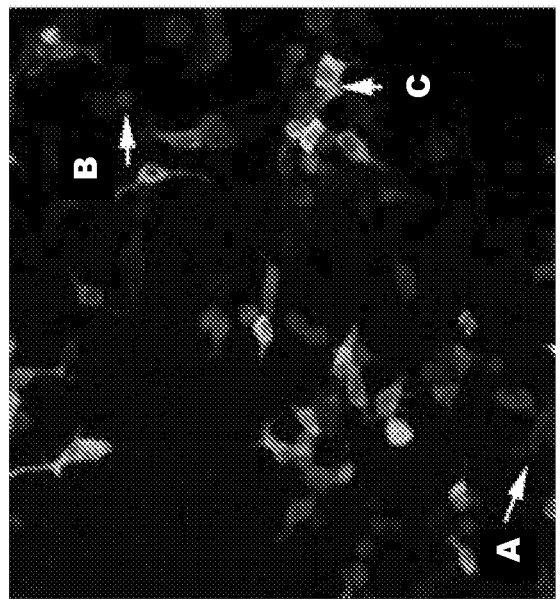
FIG. 1B  10 μM ACH

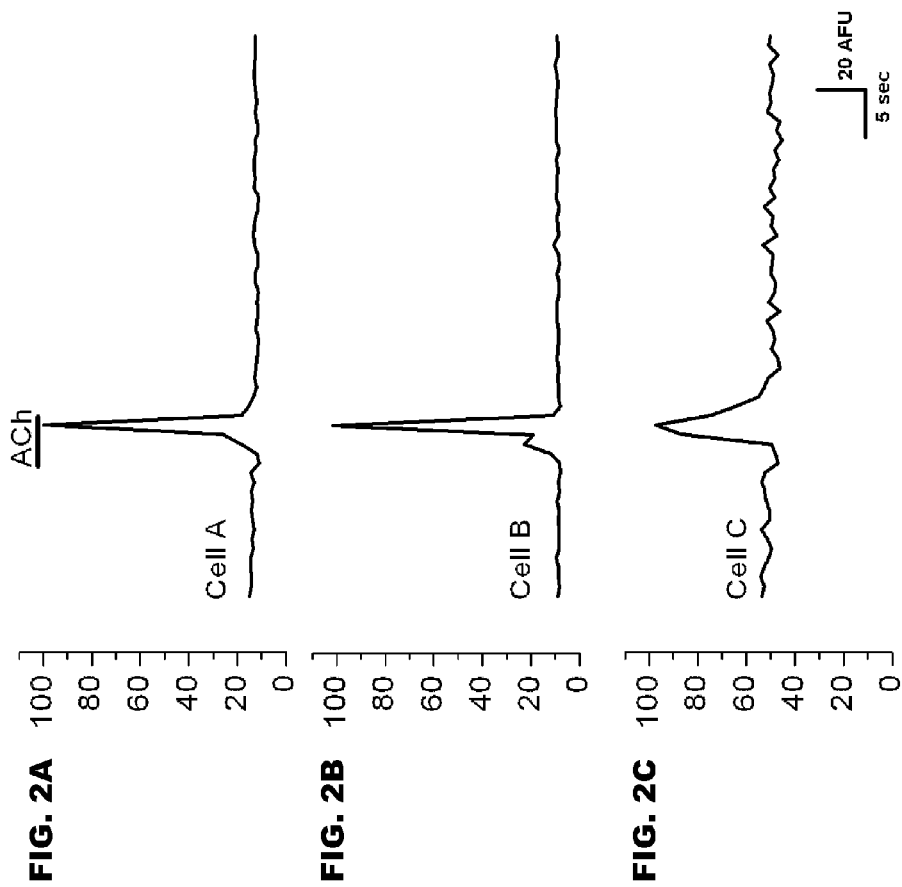

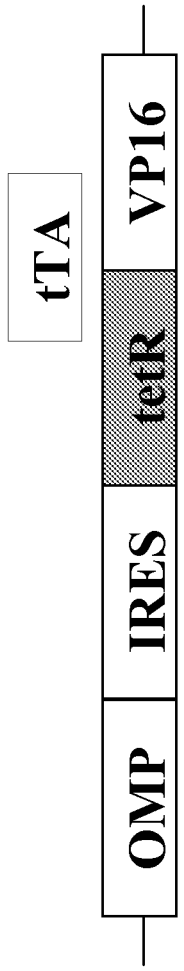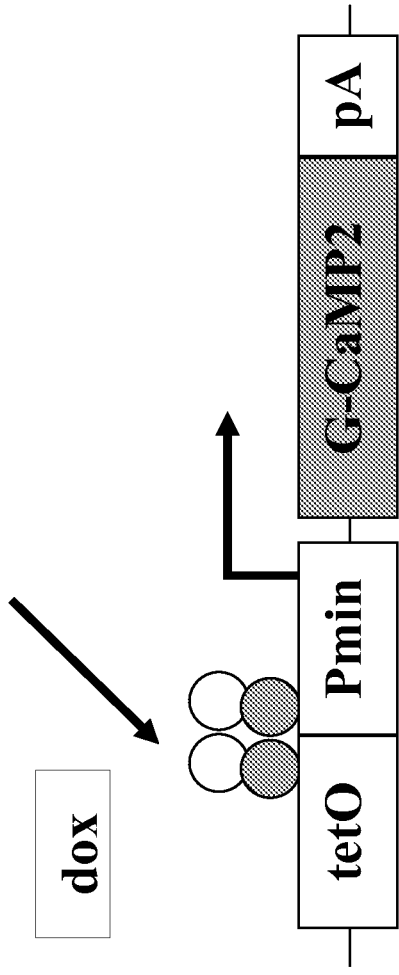
FIG. 3A
FIG. 3B

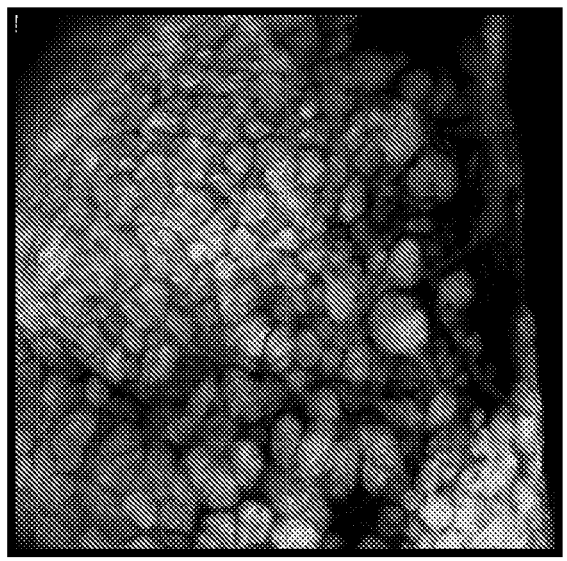
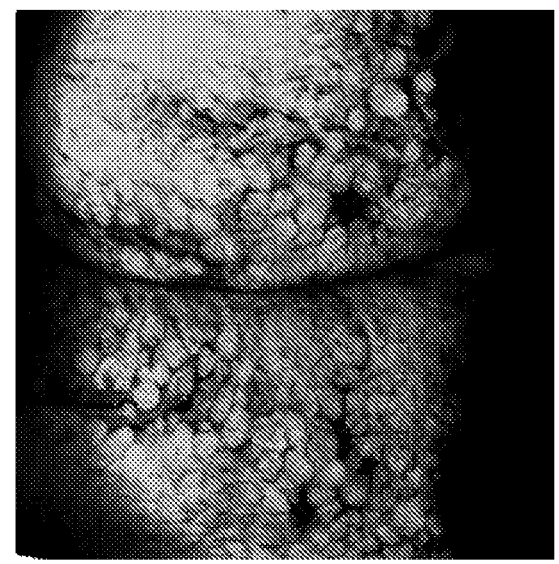
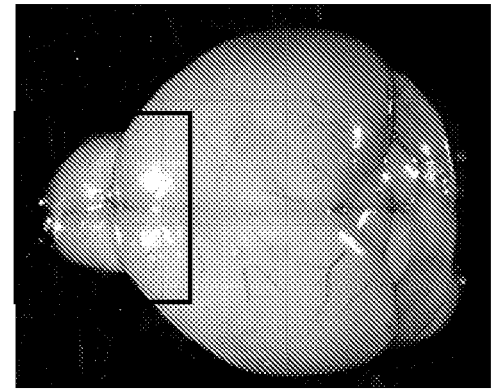
FIG. 8C
FIG. 8B
FIG. 8A

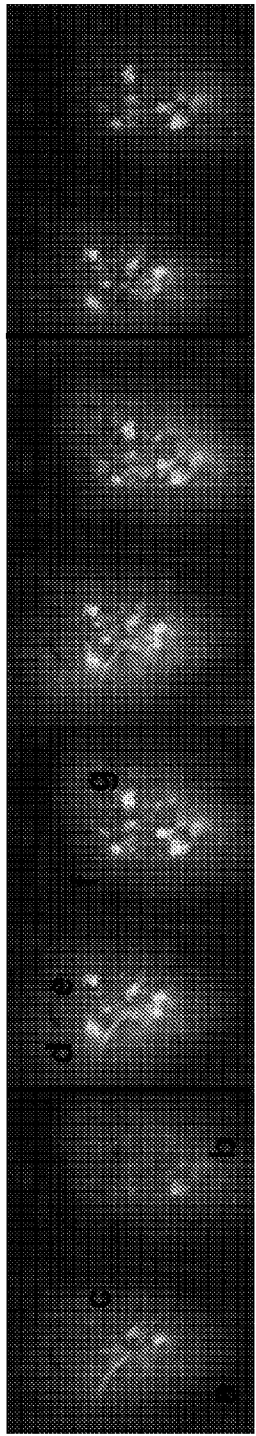
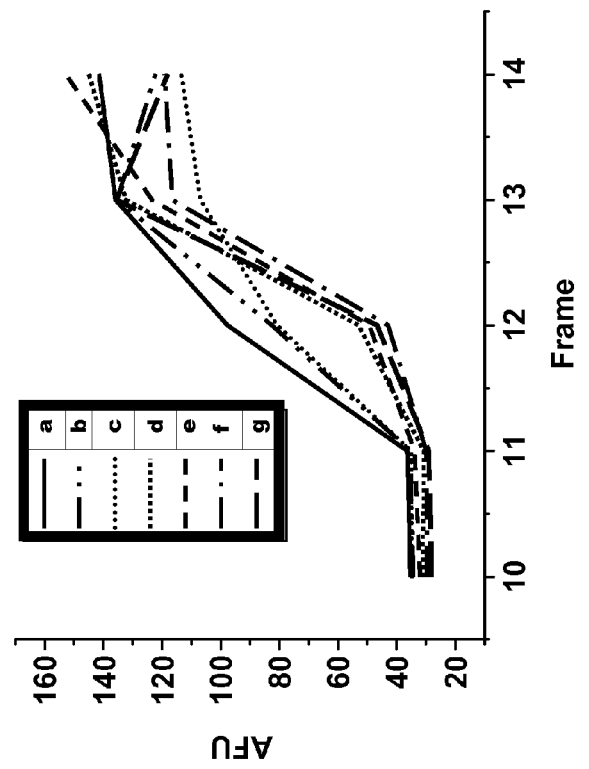

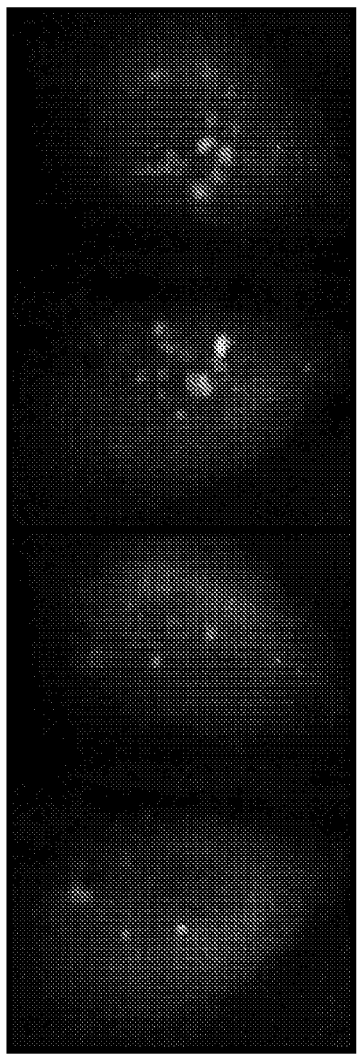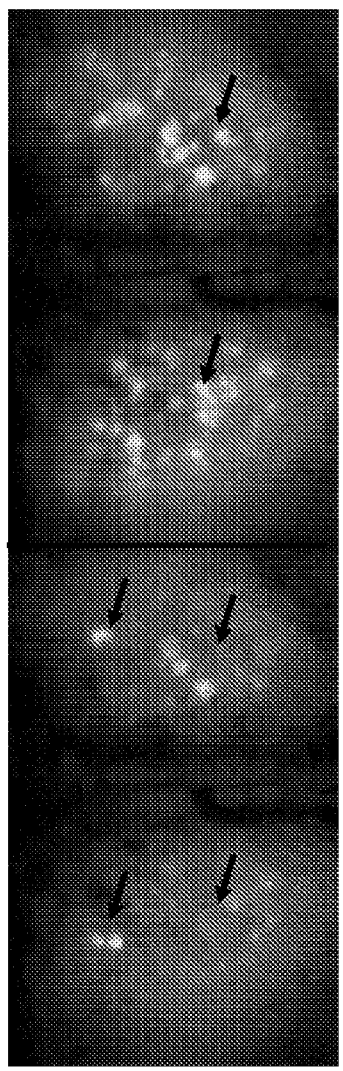

FIG. 13A

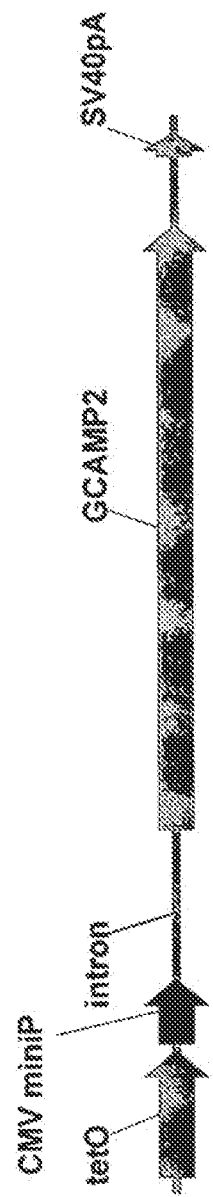

FLUORESCENT MOUSE MODEL

CROSS-REFERENCE TO RELATED APPLICATIONS

This application is the National Stage of International Application No. PCT/US2007/022611, filed Oct. 24, 2007, which claims priority to U.S. Provisional Application No. 60/863,301, filed Oct. 27, 2006.

RELATED APPLICATION

This application relates to and claims priority to U.S. Provisional Patent Application No. 60/863,301, which was filed Oct. 27, 2006 and is incorporated herein by reference in its entirety.

FEDERALLY SPONSORED RESEARCH OR DEVELOPMENT

The invention was made with government support under grant number R01DC8003 awarded by the National Institute of Deafness and other Communication Diseases (NIDCD). The government may have certain rights in the invention.

FIELD OF THE INVENTION

The present invention relates to compositions and methods for detecting and/or measuring modulation of genetically encoded sensors, e.g., sensors that detect intracellular calcium signaling. Such compositions and methods are useful, e.g., in mapping and examining fluctuations of in vivo molecules, e.g., calcium ions, within and between targeted populations of cells. Specifically, a mouse model is provided that is useful for detecting and/or measuring real-time $Ca^{2+}$ signaling in an in vivo environment.

BACKGROUND OF INVENTION

The human brain contains from 10 to 100 billion neurons, and each has hundreds of connections with neighboring neurons. Making sense of these intricate connections is essential to understanding brain function. Traditionally, electrodes have been inserted into the brain or patched on a neuron to record neuronal cell activities. Electrical signals offer high temporal resolution, but cannot provide information for a large number of cells simultaneously. Additionally, the surgical implantation of the electrodes compromises the system and requires monitoring to prevent infection.

Imaging technology has provided a means to monitor a large population of cells simultaneously. Technologies such as functional MRI, computed tomography (CT), and positron emission tomography (PET) have potential to image brain activity and body function in a noninvasive manner. But, these imaging technologies do not provide the necessary temporal and spatial resolution that is necessary to understand cellular function.

An alternative method is using optical imaging to image cell activity by recording either the calcium transients or the voltage signals by cells. Traditionally, these methods have used organic dyes that alter their optical properties in response to changes in their environment. For example, the calcium indicator fluo-4 increases its fluorescence in response to increased calcium concentration inside the cell. With these chemical indicators, cellular responses in a large number of cells can be recorded with relatively high temporal and spatial resolution. But, the loading of these dyes into tissue or live animals has been difficult. In general, these dyes must be applied by bulk-loading techniques, such as injection into the target tissues or invasive surgical manipulations. The successful use of these chemical indicators is dependent, in large part, on the successful application of the dyes to the target tissues. The use of chemical indicators is limited further by the lack of cell-type specificity.

Genetically encoded sensors (GES) have provided a means to monitor cell activity with high temporal and spatial resolution in a noninvasive manner and allow long-term studies of neuronal activity and morphology. Several fluorescent protein (FP) based indicators are available that monitor changes in calcium concentration, synaptic transmission, voltage activation, and kinase activity. Among them, the most widely used indicator belongs to the category of calcium sensors. Such calcium sensors include cameleon, Camgaroo, Troponeon, and G-CaMP (G-CaMP 1.3 and G-CaMP 1.6). G-CaMP is an engineered protein that contains a calmodulin domain and a calmodulin binding, myosin light chain, kinase, M13 peptide that flanks the circular permutated EGFP (enhanced green fluorescent protein). The binding of calcium to G-CaMP induces conformational changes of the protein and significantly increases its fluorescence when excited at 488 nm. An improved variant of G-CaMP is G-CaMP2. At physiological temperatures, G-CaMP2 fluoresces approximately 22× brighter than G-CaMP and 6× brighter than G-CaMP1.6 (Tallini, Y. N., et al., 2006). G-CaMP2 also exhibits a 4- to 5-fold increase in signal between basal calcium and saturating calcium conditions. While genetically encoded calcium sensors hold great promise for studying calcium signaling in complex organ function, they have not been effectively used in mammals in vivo because of poor intrinsic signal strength, inadequate temperature stability, or perturbing interactions between the sensing molecule and endogenous cellular proteins. Thus, there remains a need for compositions and methods for detecting and measuring, e.g., intracellular signaling in vivo.

SUMMARY OF INVENTION

The present invention overcomes these and other limitations, particularly of previously available GES, such as for example, calcium sensors, and provides a transgenic non-human animal, e.g., a transgenic mouse, that may be used to detect and/or measure, e.g., intracellular calcium signaling. Specifically, the invention provides a model that allows combinatorial targeting of specific cell populations using genetic crosses to target, e.g., a fluorescent calcium sensor, with high signal-to-noise ratio, to specific types of cells. The compositions and methods of the invention provide, e.g., various means to detect and/or measure, e.g., calcium fluctuations in specific cells through temporal regulation of, e.g., calcium sensor expression.

Thus, one embodiment of the invention is a transgenic mouse comprising a first polynucleotide comprising a GES operably linked to an inducible regulatory element and a second polynucleotide encoding a transactivator of the inducible regulatory element operably linked to a tissue-specific regulatory element, wherein expression of the GES may be detected and/or measured optionally in vivo using a noninvasive technique.

Another embodiment of the invention is a transgenic mouse comprising a first polynucleotide encoding a fluorescent $Ca^{2+}$ indicator operably linked to an inducible regulatory element and a second polynucleotide encoding a tetracycline transactivator operably linked to a tissue-specific regulatory element, wherein expression of the fluorescent Ca$^{2+}$ indicator may be detected and/or measured optionally in vivo using a non-invasive technique.

A further embodiment of the invention is a method for identifying a candidate compound that modulates intracellular calcium signaling. This method comprises providing a candidate compound, providing a transgenic mouse according to the present invention, administering the candidate compound to the transgenic mouse, and evaluating an effect, if any, of the candidate compound on intracellular calcium signaling.

BRIEF DESCRIPTION OF DRAWINGS

FIG. 1 shows the expression of G-CaMP2 in HEK293 cells containing both tetO-G-CaMP2 and VP22-tTA plasmids. Cells co-transfected with the two plasmids show fluorescence, while cells with only one of the plasmids, or neither, are not fluorescent (Control, FIG. 1A). The addition of 10 µM acetylcholine (ACH) induces a subpopulation of cells to respond with increases in fluorescence (FIG. 1B). Acetylcholine activates G-protein coupled muscarinic acetylcholine receptors and mobilizes intracellular calcium. Arrows point to three of the responsive cells (a, b, and c of both FIGS. 1A and 1B).

FIG. 2 illustrates the respective response profiles of cells a (FIG. 2A), b (FIG. 2B), and c (FIG. 2C), as shown in FIG. 1, to the addition of 10 µM acetylcholine over time. (AFU: artificial fluorescence unit).

FIG. 3 is a schematic of the transgenic approach used for the inducible expression of G-CaMP2. FIG. 3A illustrates the construct used to target the tetracycline transactivator protein (tTA) to the entire population of sensory neurons. The tTA gene (tetR and VP16) was inserted in the 3' untranslated DNA flanking the olfactory marker protein (OMP) gene such that its translation is directed by an internal ribosome entry site (IRES). Cells that activate OMP gene transcription and harbor the construct will express a bicistronic RNA encoding both OMP and tTA. In the presence of the tetracycline derivative doxycycline (dox), a conformational change in the Tet repressor (tetR) prevents the binding of tTA to tetO. FIG. 3B illustrates the construct encoding the Ca$^{2+}$ sensor, G-CaMP2, under the control of the tetracycline promoter (tetO). The tetracycline promoter includes multiple tetracycline operon enhancer sequences and a minimal promoter. Because the tetO promoter is only active in the presence of tTA protein (round molecules), G-CaMP2 is only expressed in cells that activate the OMP gene.

FIG. 8 shows the dorsal glomeruli of OMP-tTA-G-CaMP2 mice. The expression of G-CaMP2 can be detected at the gross level (FIG. 8A) and the cellular level (FIGS. 8B and 8C).

FIG. 11 shows the sequential activation of glomeruli of OMP-tTA-G-CaMP2 mice by the odor of butyraldehyde. Initially, few glomeruli are activated (FIG. 11A). Over time, more glomeruli become activated (FIGS. 11B, 11C, and 11D). The fluorescence intensity of glomeruli a, b, c, d, e, f, and g consistently increases over the course of odor exposure (FIG. 11E).

FIG. 12 shows the activation of different glomeruli in response to different odors and concentration of odors. Amyl acetate activated one set of glomeruli (FIG. 12A), while butyraldehyde activated another set of glomeruli (FIG. 12B). When the two odors are presented to the animal simultaneously, fewer glomeruli became activated in response to a lower concentration of $10^{-2}$ (FIG. 12C) compared to a concentration of $10^{-1}$ (FIG. 12D).

FIG. 13 shows the G-CaMP2 sequence (SEQ ID NO:1 (polynucleotide sequence) and SEQ ID NO:2 (polypeptide sequence)) and construct used to generate the TetO-G-CaMP2 mouse model of the invention. The G-CaMP2 used by the invention includes 6 HIS tags on the N-terminus and is encoded downstream of an inducible promoter and upstream of a SV40 polyA sequence (FIG. 13A and FIG. 13B). The inducible promoter contains a minimal CMV promoter (CMV miniP) regulated by 4 TetO sequences (tetO) and is separated from G-CaMP2 with a generic intron (FIG. 13B).

DETAILED DESCRIPTION

Figure 4C:
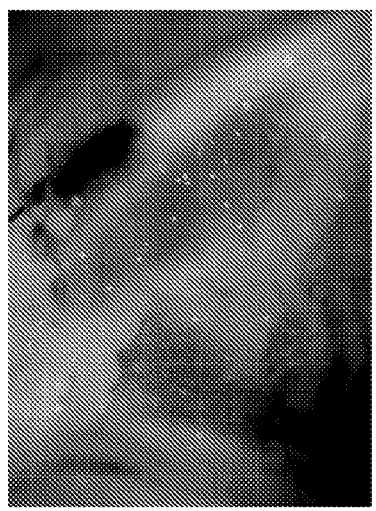
FIG. 4 shows images demonstrating the expression of G-CaMP2 in the main olfactory epithelium of compound transgenic mice bearing an OMP-IRES-tTA allele and a TetO-G-CaMP2 allele. Transgenic mice bearing an OMP-IRES-tTA allele were crossed with one of 14 founder transgenic lines of mice bearing a TetO-G-CaMP2 allele. The resultant G-CaMP2 expression of Line 1 (FIG. 4A), Line 3 (FIG. 4B), Line 4 (FIG. 4C), Line 8 (FIG. 4D), Line 5, and Line 10 (FIG. 4F) are shown. Bright dots indicate G-CaMP2 expressing neurons.

The present invention provides compositions and methods to detect and/or measure GES activation caused by, e.g., in vivo calcium (Ca$^{2+}$) signaling of specific tissues. The compositions and methods provided herein overcome the low signal-to-noise ratio and in vivo limitations associated with prior attempts to detect and/or measure, e.g., intracellular $Ca^{2+}$ signaling. Specifically, the invention allows combinatorial targeting of specific cell populations using, e.g., a tetracycline-based, inducible, modular transgenic system.

In a first embodiment of the present invention, there is provided a transgenic mouse comprising a first polynucleotide comprising a GES operably linked to an inducible regulatory element and a second polynucleotide encoding a transactivator of the inducible regulatory element operably linked to a tissue-specific regulatory element, wherein expression of the GES may be detected and/or measured optionally in vivo using a non-invasive technique.

In the present invention, the GES may be any polypeptide whose physical properties are altered so as to produce a fluorescent signal in the presence of, e.g., specific ions, metabolites or secondary messengers. For example, the GES may be a fluorescence (Forster) resonance energy transfer (FRET)-based sensor or a single fluorescent protein (FP)-based sensor.

Non-limiting examples of FRET-based sensors that may be used in the present invention include FIP-CBsm, Cameleon-2, Split Cameleon-2, Cameleon-3, YC2.0, YC4.0, YC2.1, YC3.1, YC2.3, YC2.6, YC3.12, YC3.2, YC3.3, YC3.6, YC6.1, TN-L15, TN-humTnC, TN-XL, Split indicator of cAMP, CGY-Del1, Cygnet-2, cGES-GKIB, cGES-DE2, cGES-DE5, Raichu-Ras, Raichu-Rap1, Raichu-Cdc42, Raichu-Rac1, Raichu-CRIB, Cdc42-indicator, Cdc42-GEFs-indicator, Raichu-RhoA, Raichu-RBD, ART, AKAR1, Srk-indicator, EGFR-indicator, Abl-indicator, Picchu, Aktus, BKAR, CKAR, EAS-2, EAS-3, and EAS-5. The FRET-based sensors are reviewed in, e.g., Souslova, E. A., and Chudakov, D. M., Genetically Encoded Intracellular Sensors Based on Fluorescent Proteins, Biochemistry (Moscow), 72(7):683-97 (2007).

Non-limiting examples of single FP-based sensors that may be used in the present invention include Camgaroo-1, Camgaroo-2, G-CaMP, G-CaMP1.6, G-CaMP2, Cameleon, Troponeon, Flash-Pericam, Split-Pericam, Ratiometric-Pericam, Inverse-Pericam, Case 12, Case 16, Cyan-Sinphos, Green-Sinphos, Yellow-Sinphos, and HyPer. Single FP-based sensors are reviewed in, e.g., Souslova, E. A., and Chudakov, D. M., supra.

Preferably, the FP-based sensor is a G-CaMP2 indicator. More preferably, the G-CaMP2 indicator is a polypeptide having from about 1 to about 25 His residues at its N-terminus.

In this embodiment, the regulatory elements—both inducible and tissue-specific—which are defined in further detail below, include nucleotide sequences that encode promoter regions, polyadenylation signals, transcription termination sequences, upstream regulatory domains, origins of replication, internal ribosome entry sites ("IRES"), mRNA, enhancers, splice junctions, and other elements known in the art, which collectively provide for the replication, transcription, post-transcriptional processing and translation of a coding sequence in a recipient cell. Not all of these regulatory elements need always be present so long as the selected coding sequence is capable of being replicated, transcribed and translated in an appropriate host cell/tissue.

By "enhancer sequence" is meant a nucleic acid sequence that, when positioned proximate to a promoter, confers increased transcription activity relative to the transcription activity resulting from the promoter in the absence of the enhancer domain. Accordingly, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

In the present invention, the inducible regulatory element includes at least a polynucleotide sequence selected from a tetracycline- or tetracycline derivative-regulated promoter, a steroid-regulated promoter, and a metal-regulated promoter. Non-limiting examples of inducible regulatory elements that may be used in the present invention include polynucleotide sequences that include at least a tetracycline-responsive promoter, a doxycycline-responsive promoter, aminocycline-responsive promoter, a metallothionine-responsive promoter, an ecdysone-responsive promoter, other steroid-responsive promoters, a rapamycin-responsive promoter, an interferon regulated promoter, a progesterone receptor-derived promoter, and an estrogen receptor derived promoter. Preferably, the inducible regulatory element is regulated by a tetracycline transactivator, such as for example a tTA or a rtTA, as disclosed in further detail below.

In this embodiment, the tissue-specific regulatory element targets expression of the GES to a desired tissue and/or cell type. In the present invention, the tissue-specific regulatory element may target expression of the GES to, e.g., neural, epithelial, muscular, connective, brain, skin, intestine, pancreas, kidney, lung, stomach, liver, retinal, esophagus, colon, prostate, ovary, bladder, uterus, and bone. Preferably, the tissue-specific regulatory element targets expression of the GES to neural or brain tissue.

Tissue-specific regulatory elements, e.g., promoters, are well know in the art and may be used in accordance with the present invention so long as the regulatory element is effective to target and express a polynucleotide of interest (which encodes the transactivator) in a selected tissue and/or cell type. Representative, non-limiting examples of such tissue-specific regulatory elements are set forth below:

Neural

The tissue-specific regulatory element may include a neuronal promoter. Preferably, the tissue-specific regulatory element provides specific expression in the central nervous system (CNS). One example of such a neural-specific regulatory element is the mouse Thy1 promoter (Ingraham, H. A., Lawless, G. M., Evans, G. A. (1986) The mouse Thy-1.2 glycoprotein gene: complete sequence and identification of an unusual promoter. J. Immunol. 136, 1482-1489). Other non-limiting examples of a neural-specific regulatory element include a BDNF promoter, a NGF promoter, a growth factor promoter, an axon-specific promoter, a dendrite-specific promoter, a brain-specific promoter, and a hippocampal-specific promoter. Another example of a neuron-specific promoter is a neurofilament promoter (Byrne et al., 1989).

Brain

Non-limiting examples of brain-specific regulatory elements include glial fibrillary acidic protein (GFAP) promoter, Brenner M, Kisseberth W C, Su Y, Besnard F, Messing A., GFAP promoter directs astrocyte-specific expression in transgenic mice. J. Neurosci. 1994; 14: 1030-1037; brain-specific promoter of the human FGF1 gene, Oncogene. 2000 Dec. 14; 19(54):6229-39. Tumorigenesis in transgenic mice in which the SV40 T antigen is driven by the brain-specific FGF1 promoter. Chiu I M, Touhalisky K, Liu Y, Yates A, Frostholm A.; calcium-calmodulin-dependent kinase II (CamKII) promoter, Science. 1996 Dec. 6; 274(5293):1678-83. Control of memory formation through regulated expression of a CaMKII transgene. Mayford M, Bach M E, Huang Y Y, Wang L, Hawkins R D, Kandel E R; portions of the murine Cyp19 gene promoter, J Steroid Biochem Mol. Biol. 2007 February; 103(2):119-28., Epub 2006 Oct. 31, 0.2-kb promoter sequence of the murine Cyp19 gene target beta-galactosidase expression to specific brain areas of transgenic mice. Nausch N, Manteuffel G, Vanselow J; portions of the SCN8A promoter, Mamm Genome. 2007 Oct. 9; Identification of evolutionarily conserved, functional noncoding elements in the promoter region of the sodium channel gene SCN8A. Drews V L, Shi K, de Haan G, Meisler M H; neuregulin 1 (NRG1) type IV promoter, J Biol. Chem. 2007 Aug. 17; 282(33):24343-51., Epub 2007 Jun. 12., Molecular cloning of a brain-specific, developmentally regulated neuregulin 1 (NRG1) isoform and identification of a functional promoter variant associated with schizophrenia. Tan W, Wang Y, Gold B, Chen J, Dean M, Harrison P J, Weinberger D R, Law A J.; rodent beta-adducin promoter, Nucleic Acids Res. 2006 Jan. 9; 34(1):243-53. Print 2006. Brain-specific promoter and polyadenylation sites of the beta-adducin pre-mRNA generate an unusually long 3'-UTR. Costessi L, Devescovi G, Baralle F E, Muro A F.; promoter of exon 1f of aromatase, J Steroid Biochem Mol Biol. 2005 May; 95(1-5):49-55. Analysis of spatiotemporal regulation of aromatase in the brain using transgenic mice. Harada N, Honda S., and J Steroid Biochem Mol Biol. 2001 December; 79(1-5):255-60. Characterization and purification of a protein binding to the cis-acting element for brain-specific exon 1 of the mouse aromatase gene. Honda S I, Matsumoto T, Harada N.; promoter of brain-specific angiogenesis inhibitor 1-associated protein, FEBS Lett. 2004 May 21; 566(1-3):87-94. The promoter of brain-specific angiogenesis inhibitor 1-associated protein 4 drives developmentally targeted transgene expression mainly in adult cerebral cortex and hippocampus. Kim M Y, Ahn K Y, Lee S M, Koh J T, Chun B J, Bae C S, Lee K S, Kim K K.; mouse 14-3-3 eta chain promoter, Brain Res Mol Brain Res. 2002 Apr. 30; 100(1-2):13-20. Isolation and structure of the mouse 14-3-3 eta chain gene and the distribution of 14-3-3 eta mRNA in the mouse brain. Toyooka K, Muratake T, Watanabe H, Hayashi S, Ichikawa T, Usui H, Washiyama K, Kumanishi T, Takahashi Y.; portions of CD80 promoter, Biochim Biophys Acta. 2000 Feb. 29; 1490(3):342-7. Expression of CD80 promoter in transgenic mice. Zhang H, Haasch D, Patterson B, Dickinson B, Okasinski G F.; portions of the rat aldolase C gene promoter, J. Biol. Chem., Vol. 269, Issue 6, 4194-4200, February, 1994. Analysis of a brain-specific isozyme. Expression and chromatin structure of the rat aldolase C gene and transgenes. I Makeh, M Thomas, J P Hardelin, P Briand, A Kahn and H Skala; portions of the myelin basic protein promoter, EMBO J. 1990 October; 9(10):3101-8. Core promoter of the mouse myelin basic protein gene governs brain-specific transcription in vitro. Tamura T, Sumita K, Hirose S, Mikoshiba K.; tyrosine hydroxylase promoter, J. Neurosci. 1992 November; 12(11):4460-7: 5' flanking sequences of the rat tyrosine hydroxylase gene target accurate tissue-specific, developmental, and transsynaptic expression in transgenic mice. Banerjee S A, Hoppe P, Brilliant M, Chikaraishi D M.

Muscle

Non-limiting examples of muscle-specific regulatory elements include muscle creatine kinase promoter, Mol Cell Biol. 1988 July; 8(7):2896-909. Identification of upstream and intragenic regulatory elements that confer cell-type-restricted and differentiation-specific expression on the muscle creatine kinase gene. Sternberg E A, Spizz G, Perry W M, Vizard D, Weil T, Olson E N.; portions of Duchenne muscular dystrophy gene promoter, H J Klamut, S B Gangopadhyay, R G Worton and P N Ray, Mol Cell Biol. 1990 January; 10(1): 193-205, Molecular and functional analysis of the muscle-specific promoter region of the Duchenne muscular dystrophy gene; promoters of the MyoD gene family, Science. 1991 Feb. 15; 251(4995):761-6. The myoD gene family: nodal point during specification of the muscle cell lineage. Weintraub H, Davis R, Tapscott S, Thayer M, Krause M, Benezra R, Blackwell T K, Turner D, Rupp R, Hollenberg S, et al.; myocyte-specific enhancer binding factor MEF-2, Mol Cell Biol. 1991 October; 11(10):4854-62. Myogenin induces the myocyte-specific enhancer binding factor MEF-2 independently of other muscle-specific gene products. Cserjesi P, Olson E N.; portions of human alpha-skeletal actin gene promoter, Mol Cell Biol. 1987 November; 7(11):4089-99. Multiple 5'-flanking regions of the human alpha-skeletal actin gene synergistically modulate muscle-specific expression. Muscat G E, Kedes L.; tryponin C promoter, Gene Expr. 1993; 3(1):11-25. Tissue-specific restriction of skeletal muscle troponin C gene expression. Gahlmann R, Kedes L.

A preferred class of muscle-specific regulatory elements is the cardiac-specific regulatory elements. Cardiac-specific promoters include, but are not limited to, promoters from the following genes: an alpha-myosin heavy chain gene, e.g., a ventricular alpha-myosin heavy chain gene, a beta-myosin heavy chain gene, e.g., a ventricular beta-myosin heavy chain gene, a myosin light chain 2v gene, e.g., a ventricular myosin light chain 2 gene, a myosin light chain 2a gene, e.g., a ventricular myosin light chain 2 gene, a cardiomyocyte-restricted cardiac ankyrin repeat protein (CARP) gene, a cardiac alpha-actin gene, a cardiac m2 muscarinic acetylcholine gene, ANP gene, a BNP gene, a cardiac troponin C gene, a cardiac troponin I gene, a cardiac troponin T gene, a cardiac sarcoplasmic reticulum Ca-ATPase gene, a skeletal alpha-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

Other sources for promoters and/or enhancers are promoters and enhancers from the Csx/NKX 2.5 gene, titin gene, alpha-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

Tissue-specific enhancers may also be employed. For instance, a preferred atrial-specific enhancer is the cGATA-6 enhancer. In other embodiments, the enhancer is not tissue-specific.

Skin

Non-limiting examples of regulatory elements directing skin-specific transgene expression include keratin promoters such as a K5 promoter, a K6 promoter, or a K14 promoter, or a fragment thereof. These promoters have been used to generate transgenic mice with skin-specific transgene expression (Cataisson et al., J Immunol 171:2703-2713 (2003); Shibaki et al., J Invest Dermatol 123:109-115 (2004); Feith et al., Cancer Res 61:6073-6081 (2001) Vassar et al., Proc Natl Acad Sci USA 86:1563-1567 (1989)). Additionally, U.S. Pat. No. 5,811,634 discloses the use of promoter/regulatory sequences of a K1 promoter, a K5 promoter, a K6 promoter and a K10 promoter to direct transgene expression to the cells of the skin in a transgenic non-human mammal.

Esophagus

A non-limiting example of a regulatory element directing esophagus-specific transgene expression is an Epstein-Barr virus (EBV) ED-L2 promoter, or a fragment thereof. The EBV ED-L2 promoter has been used to express a transgene in the cells of the esophagus of transgenic mice (Opitz et al., J Clin Invest 110:61-769 (2002); Fong et al., Cancer Res 63:4244-4252 (2003)).

Liver

Non-limiting examples of regulatory elements directing liver-specific transgene expression are a major urinary protein (MUP) promoter, or a fragment thereof, an albumin promoter, or a fragment thereof, a transthyretin promoter, or a fragment thereof, an apoE promoter, or a fragment thereof, or a phenylalanine hydroxylase promoter, or a fragment thereof. These promoters have been used to generate transgenic mice with transgene expression directed to the cells of the liver (Kawamure et al., Hepatology 25:1014-1021 (1997); Kuklin et al., Mol Cancer 3:17-27 (2004); Nicolas et al., Proc Natl Acad Sci USA 99:4596-4601 (2002); FEBS Lett 555:528-532 (2003); Jackerott et al., Diabetologia 45:1292-1297 (2002)).

Colon

Non-limiting examples of regulatory elements directing colon-specific transgene expression are a villin promoter, or a fragment thereof and a fatty acid binding protein promoter (FABP), or a fragment thereof. These promoters have been used to generate transgenic mice with colon-specific transgene expression (Pinto et al., J Biol Chem 274:6476-6482 (1999); Janssen et al., Gastroenterology 123:492-504 (2002); Sweetser et al., Proc Natl Acad Sci 85:9611-9615 (1988); Cobb et al., Cancer 100:1311-1323 (2004)). U.S. Application Publication No. US 2003/0177516 discloses the use of the intestinal FABP promoter region to direct transgene expression to the cells of the gut in a transgenic bird.

Prostate

Non-limiting examples of regulatory elements directing prostate-specific transgene expression are a cryptdin-2 promoter, or a fragment thereof, a prostate-specific antigen (PSA) promoter, or a fragment thereof, a C(3)1 promoter, or a fragment thereof, a prostate secretory protein of 94 amino acids (PSP94) promoter, or a fragment thereof, and a probasin promoter, or a fragment thereof. These promoters have been used to generate transgenic mice with prostate-specific transgene expression (Garabedian et al., Proc Natl Acad Sci USA 95:15382-15387 (1998); Cleutjens et al., Mol Endocrinol 11:1256-1265 (1997); Zhang et al., Prostate 443:278-285 (2000); Gabril et al., Gene Ther 9:1589-1599 (2002); Masumori et al., Cancer Res 61:2239-2249 (2001)). U.S. Pat. No. 6,136,792 discloses the use of promoter/regulatory sequences of the PSA promoter to direct transgene expression to the cells of the prostate in a transgenic non-human mammal. Additionally, U.S. Pat. Nos. 5,952,488 and 5,907,078 disclose the use of the probasin promoter to drive expression of a transgene specifically in the prostate of transgenic non-human mammals.

Ovary

A non-limiting example of a regulatory element directing ovary-specific transgene expression is the ovarian-specific promoter (OSP-1) or a fragment thereof. This promoter has been used to express a transgene in the cells of the ovaries of transgenic mice (Garson et al., J Soc Gynecol Investig 10:244-250 (2003)).

Kidney

Non-limiting examples of regulatory elements directing kidney-specific transgene expression are the uromodulin promoter, or a fragment thereof, the Tamm-Horsfall protein (THP) promoter, or a fragment thereof, and the type 1 gamma-glutamyl transpeptidase promoter, or a fragment thereof. These promoters have been used to generate transgenic mice with kidney-specific transgene expression (Huang et al., BMC Biotechnol 5:9 (2005); Zhu et al., Am J Physiol Renal Physiol 282:F608-F617 (2002); Terzi et al., J Clin Invest 106:225-234 (2000)). U.S. Pat. No. 6,888,047 discloses the use of the uromodulin promoter to direct transgene expression to the cells of the kidneys in a transgenic non-human mammal. Another example of a kidney-specific promoter is the Ksp-cadherin promoter (Yun Bai, et al., 2002) or the Sglt2 promoter (Rubera I, et al., 2004).

Bladder

Non-limiting examples of regulatory elements directing bladder- or urothelium-specific transgene expression are the promoters, or fragments thereof, directing expression of the uroplakin genes. The uroplakin II promoter has been used to engineer transgenic mice with transgene expression specifically in urothelium of the bladder (Cheng Cancer Res 62: 4157-4163 (2002); Lin et al., Proc Natl Acad Sci USA 92:679-683 (1995)). U.S. Pat. Nos. 5,824,453 and 6,001,646 disclose the use of the uroplakin II gene promoter to produce transgenic animals expressing a transgene specifically in the cells of the bladder urothelium. Furthermore, U.S. Pat. No. 6,339,183 discloses transgenic animals in which the urothelium-specific expression of a transgene is directed by a uroplakin Ia promoter, a uroplakin mi promoter, or a urohingin promoter.

Uterus

A non-limiting example of a regulatory element directing uterus-specific transgene expression is the uteroglobin promoter, or fragments thereof. This promoter has been used to engineer transgenic mice with transgene expression specifically in the uterus (Gomez Lahoz et al., Gene 117:255-258 (1992); Sandmoller et al., 9:2805-2815 (1994)).

Additional exemplary tissue-specific regulatory elements include, but are not limited to, albumin promoters (liver specific; Pinkert et al., 1987), lymphoid specific promoters (Calame et al., 1988), promoters of T-cell receptors (Winoto et al., 1989) and immunoglobulins (Baneriji et al., 1983; Queen and Baltimore, 1983), intestine-specific promoters (Fabp promoter, Bullard, D. C., et al., 2002), pancreas-specific promoters (Edlunch et al., 1985), or mammary gland-specific promoters (milk whey promoter, U.S. Pat. No. 4,873,316). Developmentally-regulated promoters may also be used, such as the murine homeobox promoters (Kessel et al., 1990) or the alpha-fetoprotein promoter (Campes et al., 1989).

In a preferred embodiment, the tissue-specific regulatory element includes the OMP promoter.

In another embodiment of the present invention, there is provided a transgenic mouse comprising a first polynucleotide encoding a fluorescent $Ca^{2+}$ indicator operably linked to an inducible regulatory element and a second polynucleotide encoding a tetracycline transactivator operably linked to a tissue-specific regulatory element. In this embodiment, expression of the fluorescent $Ca^{2+}$ indicator may be detected and/or measured optionally in vivo using a non-invasive technique.

In the present invention, the GES, e.g., fluorescent $Ca^{2+}$ indicator, preferably is G-CaMP2. It is also preferred that the inducible regulatory element comprises a tetracycline promoter and that the tissue specific regulatory element comprises an olfactory marker protein (OMP) promoter.

The GES, e.g., fluorescent $Ca^{2+}$ indicator, is detected or measured using conventional methods known in the art and/or as disclosed further herein. As used herein, "detected," "detection," and the like are intended to mean determining whether the GES, e.g., fluorescent $Ca^{2+}$ indicator, has been activated by the presence of, e.g., $Ca^{2+}$. As used herein, "measured," measuring," and the like are intended to mean monitoring the level of activation and/or quantitating the level of activation of the GES, e.g., $Ca^{2+}$ indicator, and relating that to the concentration of, e.g., $Ca^{2+}$.

Such detection and/or measuring may be carried out in vivo using invasive or non-invasive procedures. As used herein, invasive procedures include modifying the animal to enhance detection and/or measurement of a signal generated by the GES, e.g., fluorescent $Ca^{2+}$ indicator, of the present invention. Invasive procedures include, e.g., thinning the skull of the animal, e.g., transgenic mouse, using conventional methods known in the art and disclosed in more detail herein. Additionally, tissue samples from the transgenic animal, e.g., mouse, may be manipulated ex vivo, in situ, or in vitro. For example, a signal from a GES, e.g., a fluorescent $Ca^{2+}$ indicator, from a brain slice of a transgenic mouse according to the present invention may be detected and/or measured using conventional methods, including those disclosed herein.

As used herein, non-invasive procedures include non-surgical and/or minimally invasive procedures for positioning, detecting, and/or measuring a signal generated by a GES, e.g. a fluorescent $Ca^{2+}$ indicator, of the present invention.

Another embodiment of the invention is a method for identifying a candidate compound that modulates intracellular calcium signaling. This method comprises providing a candidate compound, providing a transgenic mouse according to the present invention, administering the candidate compound to the transgenic mouse, and evaluating an effect, if any, of the candidate compound on intracellular calcium signaling.

In this embodiment, "modulates," "modulation," and the like means either an increase or decrease in intracellular calcium signaling compared to a transgenic mouse treated with a control. In the present invention, "candidate compound" is to be broadly interpreted and includes a biological and/or non-biological agent. For example, the candidate compound may be a nucleic acid, polypeptide, polysaccharide, or small organic or inorganic molecule. Candidate compounds may include a fusion protein, an antibody, antibody mimetic, domain antibody, targeted aptamer, RNAi, siRNA, shRNA, or an antisense sequence.

The candidate compound may be administered to the transgenic mouse in any convenient manner. For example, the candidate compound may be administered to the transgenic mouse orally, parenterally, sublingually, transdermally, rectally, transmucosally, topically, via olfaction, via buccal administration, or combinations thereof. Parenteral administration may be intravenous, intraarterial, intraperitoneal, subcutaneous, intramuscular, intrathecal, or intraarticular. Preferably, the candidate compound is administered to the transgenic mouse through olfaction. As used herein, administration through olfaction means that the candidate compound is presented to the transgenic mouse in such a manner that the candidate compound is inhaled.

In another aspect of the invention, the candidate compound may be administered to the transgenic mouse by delivering it directly to a tissue sample. For example, a brain slice from a transgenic mouse according to the present invention may be bathed in a solution containing the candidate compound. Other analogous methods well known in the art may be used as well.

In this embodiment, evaluating an effect, if any, of the candidate compound on intracellular calcium signaling means determining whether the candidate compound increased, decreased, or had no effect on intracellular calcium signaling in a specific tissue, such as, e.g., the olfactory bulb (OB), main olfactory epithelium (MOE), or vomeronasal organ (VNO). Methods for carrying out such evaluations are known in the art and disclosed further herein.

In this embodiment, the evaluation step may be carried out in vivo, through a tissue of the transgenic mouse in a non-invasive procedure as disclosed previously. Preferably, the non-invasive procedure is carried out through the skull of the transgenic mouse without thinning or otherwise decreasing the thickness of the skull.

Alternatively, the evaluation step may be carried out in vivo through a tissue of the transgenic mouse in a more invasive procedure by, e.g., thinning or otherwise decreasing the thickness of the skull. Procedures for thinning the skull of a mouse are known in the art and further disclosed in the Examples below. Preferably, in this aspect of the invention, the thickness of the skull at a particular site is decreased by, e.g. shaving the skull as disclosed herein, to a thickness less than about 150 µm, preferably less about than 100 µm, more preferably less than about 75 µm, such as for example between about 40-60 µm, including 50 µm.

In this embodiment, the evaluating step may also be carried out on tissue obtained from the brain of a transgenic mouse according to the present invention. For example, the evaluating step may be carried out on a brain slice.

Tetracycline Inducible System

The present invention will now be described with reference to a preferred embodiment that exemplifies a tetracycline-based inducible system. The tetracycline (tet) inducible system uses regulatory elements from the Tn10-encoded tetracycline resistance operon from $E.\ coli$ that can be regulated by tet. The tetracycline inducible system utilized by the invention includes two components: 1) a transactivator protein (tTA) to regulate gene expression and 2) an inducible regulatory element containing multiple tetracycline resistance operon (tetO) sequences placed upstream of a gene of interest. The tetracycline transactivator protein is a chimeric protein that consists of a fusion between the herpes simplex virus-transactivating domain VP16 and the tetracycline repressor from $E.\ coli$. The function of a tTA is to be sensitive to tetracycline and tetracycline derivatives. Such derivatives include doxycycline and minocycline. In the absence of tet or a derivative, tTA binds to the tetO sequences upstream of the gene of interest and activates transcription. In the presence of tet or a derivative, a conformational change in the tetracycline repressor prevents the binding of tTA to tetO and prevents transcription. This system has been used both in vitro and in vivo (Fruh et al. 1994; Wimmel et al. 1994; Furth et al. 1994; and Kistner et al. 1996, all incorporated herein by reference). Alternatively, a reverse transactivator (rtTA), which binds a tetO sequence in the presence of tet, may also be used in place of tTA. A skilled artisan will appreciate that the transactivator used depends upon the intended use of the invention.

In the present invention, the two components of the tet inducible system may be provided in two separate modules. The term "module", as used herein, refers to a subject having within its genome one component, or construct, that is part of a multi-component, or construct, system. One module provides the transactivator protein targeted to specific tissues of an organism (e.g., OMP-tTA line), and the other module provides the fluorescent $Ca^{2+}$ indicator G-CaMP2 under the control of a tetracycline inducible promoter (G-CaMP2 line). A skilled artisan will recognize that these modules extend the versatility of the invention by providing an interchangeable tissue-targeting component. The modules may be any subject, organism, or animal having a central nervous system. Suitable modules include: mammals, humans, mice, rats, dogs, cats, cattle, swine, sheep, and ungulates; preferably the modules are mice or rats; and more preferably the modules are mice.

Calcium Sensor Module

The first module of the present invention is exemplified by a tetracycline inducible system, which includes a transgenic mouse that harbors a GES, e.g., a fluorescent $Ca^{2+}$ indicator protein (FCIP), encoded downstream of a tet inducible promoter containing tetO sequences. The FCIP, G-CaMP2 (provided by J. Nakai, Laboratory for Memory and Learning, Saitama, Japan), was cloned downstream to the tet inducible promoter using molecular cloning methods known in the art (see, Current Protocols in Molecular Biology, Unit 1.5, pub, John Wiley & Sons, Inc., 1998 and incorporated herein by reference). The resulting nucleic acid was used to generate a transgenic mouse line by introducing the transgene-encoding nucleic acid sequence into the male pronuclei of a fertilized oocyte (e.g., by microinjection, retroviral infection, or other suitable techniques). The oocyte was placed in a pseudo-pregnant female foster animal and allowed to develop into a viable animal. Methods for generating transgenic animals via embryo manipulation and microinjection, particularly animals such as mice, have become conventional in the art and are disclosed, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, and N.Y. The TetO-G-CaMP2 transgenic mouse may be crossed with any mouse targeting the activating tTA to a specific tissue in order to evaluate calcium fluctuations and responses in the desired target tissue. For example, the TetO-G-CaMP2 transgenic mouse may be crossed with a mouse targeting tTA to the skin to study calcium fluctuations of keratinocytes as they differentiate or with a mouse targeting tTA to motor neurons to study their communication.

The FCIP encoded by the transgene is G-CaMP2, which is a variant of G-Camp. G-CaMP2 contains several mutations and alterations that enhance folding, stability, and fluorescence at physiological temperatures compared to Camp. Nevertheless, expression of G-CaMP2 in vivo has been varied. For example, modest success was achieved in mouse heart muscle by combining surgical exposure of the heart with monitoring G-CaMP2 expression (Tallini, Y. N., et al., 2006). Invasive surgery or sacrifice was required to monitor expression. In an alternative system, G-CaMP2 was used to study calcium signaling in cerebellar parallel fibers of the mouse brain (Diez-Garcia, J., et al., 2005). Temporal control of expression was not achieved in the Diez-Garcia brain model and monitoring could only be achieved in vitro.

Figure 9A:
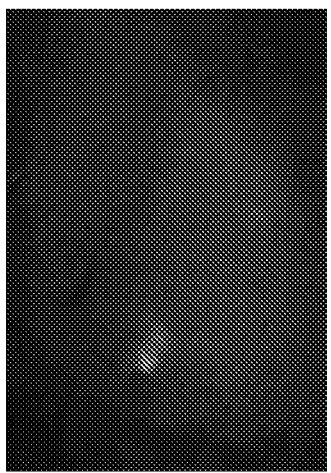
FIG. 9 demonstrates activated sensory neurons through the un-thinned skull of OMP-tTA-G-CaMP2 mice in response to different odors. Different sensory neurons are activated by amyl acetate (FIG. 9A), than those activated by butyraldehyde (FIG. 9B), or hexanoic acid (FIG. 9C).
Figure 9B:
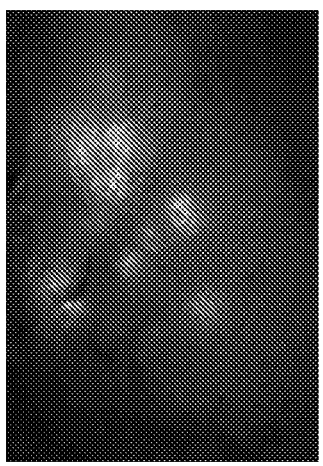

The present invention overcomes the deficiencies of the previous models by achieving much greater intensity of expression such that G-CaMP2 expression can be advantageously monitored in vivo without animal sacrifice or invasive, life-threatening, surgical procedures (see, e.g., FIGS. 9 and 10). Not wishing to be bound by a particular theory, it is possible that the robust expression of the present invention is, in part, due to the particular regulatory element and overall configuration used to create the construct used. A skilled artisan will recognize the difficulty associated with generating mice that express, e.g., a $Ca^{2+}$ sensor at a level to detect the sensor through an opaque tissue such as the bone. Neither the heart model (Tallini, Y. N., et al., 2006) nor the brain model (Diez-Garcia, J., et al., 2005) achieved the high expression necessary for detection through an opaque tissue.

The invention provides high expression capable of real-time detection that is a vast improvement over other models described in the art. Further, the G-CaMP2 transgenic mouse of the invention not only can be temporally controlled, but it may also be combined with interchangeable transgenic mice targeting a tetracycline transactivator (tTA or rtTA) to a specific tissue or population of cells to produce compound transgenic mice in which $Ca^{2+}$ signaling may be studied in a multitude of targeted tissues or cells.

Figure 13A:
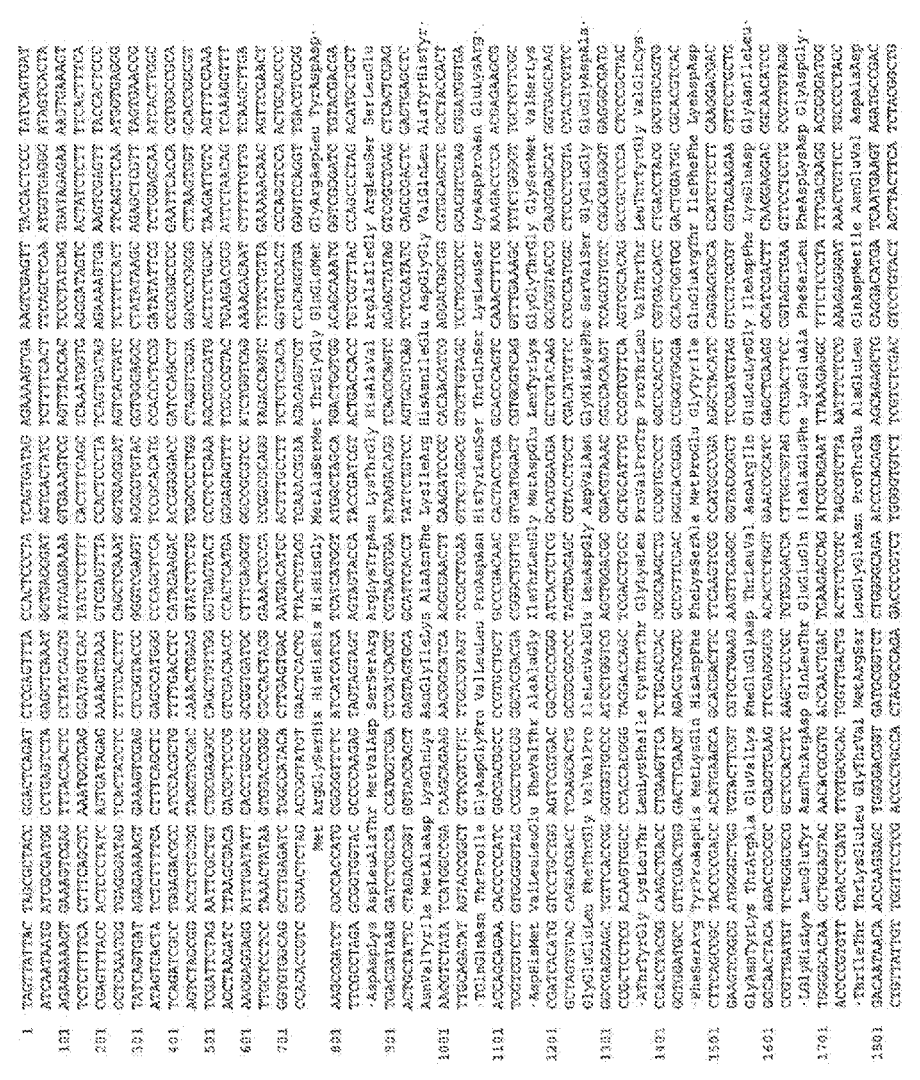

The high expression may be the result of using a CMV minimal promoter regulated by 4 tetO sequences to drive G-CaMP2 expression, the addition of 6 HIS tags to the N-terminus of G-CaMP2, or the combination of the two (see, FIGS. 13A and 13B). One skilled in the art will appreciate that the expression level achieved by the invention may be improved or lessened with the addition or removal of one or more HIS tags or regulatory tetO sequences. For example, at least 1, 2, 3, 4, 5, 6, 7, 8, 9, 10, 11, 12, 13, 14, 15, 16, 17, 18, 19, 20, 21, 22, 23, 24, or even 25 HIS tags, or respectively tetO sequences, may be useful to either increase or decrease expression such that it is measurable above background autofluorescence. Likewise, a different minimal promoter regulated by the tetO sequences may also be used to alter the expression level achieved by the invention. A suitable promoter includes any ubiquitous promoter such as, but not limited to ubiquitinase, β-actin, GAPDH, β-kinesin, ROSA, and phosphoglycerate kinase promoters. A skilled artisan will also recognize that a combination of alterations may result in an overall change in expression level and the expression level desired depends upon the intended use of the invention.

Tissue Targeting Module

The second module of the tetracycline inducible system is a transgenic mouse that expresses the tTA protein in a specific tissue or population of cells. It is envisioned that tissue-specific regulatory elements that may be used with the invention include those identified above. For example, to target tTA expression to sensory neurons, the tTA gene (tetR and VP16) was inserted in the 3' untranslated DNA sequence flanking the OMP gene, such that its translation was directed by an internal ribosome entry site (IRES) (FIG. 3A). Cells that activate OMP gene transcription, express a bicistronic RNA encoding both OMP and tTA as described in Yu et al. 2004. One of skill in the art will recognize that the tTA protein can be targeted to any specific tissue by encoding it downstream of any tissue-specific regulatory element. It may also be advantageous to target the tissue ubiquitously using an ubiquitous regulatory element, particularly if a temporally-related event, such as development or reproduction, is being evaluated. A skilled artisan will recognize that the tissue-specific regulatory element could be any regulatory element known in the art and is not limited to tissue-specific or ubiquitous regulatory elements, but also may include engineered regulatory elements.

"Compound" Transgenic Mice of the Present Invention

The present invention provides a method to generate a "compound" transgenic mouse that expresses G-CaMP2 in a targeted tissue or population of cells. The invention does not extend to compound transgenic mice made or known by others or to methods or compositions using them. The compound transgenic mouse line encodes both the G-CaMP2 downstream of an inducible regulatory element and a transactivator downstream of a tissue-specific regulatory element. Exemplary inducible and tissue-specific regulatory elements provided herein are different from each other; however, depending upon the objectives to be achieved, the two promoters may be the same or variants of each other.

To produce the compound transgenic mouse line, the first module of the invention, a transgenic mouse encoding G-CaMP2 downstream of an inducible regulatory element, is combined with the second module of the invention, a transgenic mouse encoding a transactivator downstream of a tissue-specific regulatory element. The modules are combined by breeding or crossing the two mouse lines. For example, a TetO-G-CaMP2 transgenic mouse (tet-G2) may be crossed to an OMP-IRES-tTA transgenic mouse to generate an OMP-tTA-G-CaMP2 compound transgenic mouse. The resultant compound offspring may be identified through Polymerase Chain Reaction (PCR) or Southern blot screening of genomic DNA as known in the art (see, Metzger et al., 2002).

The tet-G2 containing mice may be generated by, e.g., mating C57BL/6 wildtype females to males with the tet-G2 allele. Male mice containing both tet-G2 and OIVT alleles were used to generate 300 embryos in a week. The resulting embryos have both tet-G2 (in 50% of the embryos) and OIVT (in 100% of the embryos). These tet-G2 mice have been deposited under the terms of the Budapest Treaty as disclosed in more detail below.

Transgene expression and expression patterns may be screened using methods such as protein analysis by Western blot; RNA analysis by Northern blot or quantitative RT-PCR, histological analysis, or other methods commonly practiced in the art. Depending on the transactivator used, transgene leakage may be determined by treating (for tTA) or not treating (for rtTA) compound transgenic mice with a tetracycline derivative prior to screening for transgene expression. For example, compound transgenic mice using the tTA transactivator may be treated for about 1-3 weeks with about 0.1, 0.5, 0.75, 1, 1.5, 2, 5, 7, or 10 mg/mL of doxycycline added to drinking water. An increase in transgene expression in the presence of doxycycline indicates transgene leakage. Lines that show a high level of expression with little or no leakage are preferred.

Fluorescence Intensity

An advantage to the present invention is the production of very bright fluorescence by the selected GES, e.g., G-CaMP2, in response to stimuli that allows detection and/or measurement, e.g., in vivo without invasive surgical procedures or implants. For example, fluorescence in Line 5 mice (see FIGS. 9 and 10) is easily visible through the skull to the naked eye. Thus, animals of the present invention can be used without life-threatening trauma or high risk of infection. The subject transgenic mouse, upon stimulation, shows substantially greater fluorescence intensity, or brightness, in a cell with an increase of calcium influx/eflux compared to a reference cell without an increase in calcium influx/eflux.

For example, a sensory neuron of an OMP-tTA-G-CaMP2 compound transgenic mouse will exhibit an increase in fluorescence intensity upon stimulation compared to a non-stimulated neuron. It is envisioned that the increase in fluorescence intensity upon stimulation is at least about 10%, at least about 20%, at least about 30%, at least about 40%, at least about 50%, at least about 60%, at least about 70%, at least about 80%, at least about 90%, at least about 100% (or two-fold), at least about 150%, at least about 2×, 3×, 4×, 5×, 10×, 15×, 20×, 25×, 30×, 40×, 50×, 75×, 100×, or more, brighter in a stimulated cell compared to a non-stimulated reference cell. Methods of detecting and/or measuring brightness or fluorescence intensity are commonly known in the art. Brightness may be detected and/or measured using techniques including, but not limited to, visual screening, spectrophotometry, spectrofluorometry, fluorescent microscopy, and fluorescence activated cell sorting (FACS).

Tracing Neuronal Circuitry

It is envisioned that the transgenic animals, e.g., mice, of the invention can be used to trace neuronal circuitry. Understanding the pattern of interconnections of specific neural cells is essential to understanding their roles in nervous system function and dysfunction. Traditionally, the connections a neuron makes have been identified using electrophysiological recordings, from histochemical techniques or through the use of anterograde or retrograde tracers that make it possible to visualize the patterns of projections of individual neurons. While these approaches have been useful to identify certain aspects of neural connectivity, their invasiveness, unavoidable confounding artifacts, limitation of resolution in space and time, and the inability to reproduce findings with great fidelity limit their utility.

The transgenic mice (e.g., OMP-tTA-G-CaMP2) of the invention utilize a sensory neuron-specific regulatory element that allows the tracing of sensory neuron connections. The mapping of neuronal circuits can be achieved by a stimulation that results in intracellular calcium fluctuations. Neural activity, following stimulation, can be monitored through fluorescence imaging and facilitates the mapping of functional neuronal circuits in the complex environment of the brain. For example, OMP-tTA-G-CaMP2 transgenic mice can be stimulated with an odor, such as acetylcholine, ethyl salicylate, 2-butanone, butyraldehyde, hexyl alcohol, butyric acid, hexonoic acid, or limonene. The odor can be presented locally in the olfactory bulb to induce the fluorescence of the G-CaMP2 sensor. The level of fluorescence intensity can be analyzed through fluorescent imaging of sectioned brain tissue or through the full thickness of the skull. Alternatively, the animals can be anesthetized and their skulls thinned to allow in vivo tracing of neuronal projections with fluorescent microscopy.

A skilled artisan will appreciate that calcium signaling can be traced in other tissues by interchanging the OMP-tTA line used to generate the OMP-tTA-G-CaMP2 compound transgenic line with another specific tissue targeting tTA mouse line. For example, a transgenic mouse line targeting tTA expression to the skin using a skin specific promoter may be crossed to the TetO-G-CaMP2 line to generate a skin specific G-CaMP2 compound mouse in which calcium signaling in the skin can be traced. Other tissues in which it will be desirable to trace calcium signaling include the kidney, muscle, intestine, and those in which cell motility, communication, or signaling is of interest.

Pathological Disease And Identification of Candidate Compounds

It is envisioned that the invention can be used to measure calcium signaling, cell communication, and cell motility in models of pathological disease or subjects having such disease. One of skill in the art will recognize that there are numerous models of disease, e.g. mouse models, that are used to study the disease process, study mechanics of the disease, and to test or screen potential therapies, including identification of candidate compounds for modulating such diseases and underlying physiological conditions as disclosed above. Such disease models include, but are not limited to, mouse models of airway hyper-responsiveness (De Sanctis et al. 1995), alcohol and morphine preference (Berretini et al. 1994; Crabbe et al. 1994), atherosclerosis (Hyman et al. 1994), epilepsy (Frankel et al. 1994), and obesity (West et al. 1994). The invention may also be used in models using other organisms having a central nervous system such as cats, dogs, rats, guinea pigs, and ungulates. A skilled artisan will recognize that many models of human disease are available including, but not limited to, those of Alzheimer's disease, Parkinson's disease, many types of cancer, retinal degeneration, inflammatory bowel disease, diabetes, autoimmunity, atherosclerosis, hypertension, and many more.

The transgenic mouse of the invention may be used in combination with any mouse model of human disease to study, e.g., the role calcium plays in that disease. The TetO- G-CaMP2 transgenic mouse may be crossed to any transgenic mouse encoding a tetracycline transactivator protein (tTA or rtTA) targeted to a specific tissue or ubiquitously expressed. The resultant compound transgenic mouse, encoding both the transactivator protein and the inducible G-CaMP2, may then be crossed to the desired mouse model of human disease. A skilled artisan will recognize that the use of a tissue-targeted or ubiquitously expressed transactivator protein depends upon the disease being studied as well as the intended use of the invention. For example, if the mouse model of human disease provides the study of polycystic kidney disease, then it may be advantageous to target the expression of G-CaMP2 to the kidney or to the specific cell of the kidney affected by polycystic kidney disease. But, if the mouse model of human disease provides the study of cancer affecting multiple tissues, then it may be advantageous to ubiquitously express G-CaMP2.

Once a mouse model of human disease has been crossed to also express inducible G-CaMP2 (MHD-G-CaMP2), it may be used to study calcium-involved events (and alterations to these events due to disease) including, but not limited to, calcium signaling, cell communication, and cell motility. Methods to study the MHD-G-CaMP2 mouse model include those disclosed herein and others known in the art. A skilled artisan will recognize that the methods used to study the MHD-G-CaMP2 mouse model depend upon the disease, targeted tissue, and the intended use of the invention.

Development

It is envisioned that the invention can be used to study, e.g., calcium signaling, signal transduction, cell communication, and cell motility in development and aging models. One of skill in the art will recognize that there are presently many models available commercially or otherwise that may be used to study the development or aging process. Exemplary models may include, but are not limited to, those that over express, inhibit, eliminate, or otherwise alter the expression (tissue-targeted or ubiquitous) of developmental regulators such as those involved in WNT signaling, Hedgehog signaling, BMP signaling, and other signaling pathways or apoptosis. The invention may be used in models using a variety of organisms having a central nervous system such as mice, cats, dogs, rats, guinea pigs, and ungulates. A preferred model is a mouse. A skilled artisan will recognize that the model selected depends upon the intended use of the invention.

The transgenic mouse of the invention may be used in combination with any mouse model to study the role of, e.g., calcium in the developmental or aging process. The TetO-G-CaMP2 transgenic mouse may be crossed to any transgenic mouse encoding a tetracycline transactivator protein (tTA or rtTA) targeted to a specific tissue or ubiquitously expressed. The resultant compound transgenic mouse, encoding both the transactivator protein and the inducible G-CaMP2, may then be crossed to the desired mouse model (MM-G-CaMP2). A skilled artisan will recognize that the use of a tissue-targeted or ubiquitously expressed transactivator protein depends upon the disease being studied as well as the intended use of the invention. For example, if the mouse model provides loss of function or over expression of a protein in only the skin, then it may be advantageous to target the expression of G-CaMP2 to the skin or a specific cell of the skin. But, if the mouse model provides the loss of function or over expression of a protein in multiple tissues, then it may be advantageous to ubiquitously express G-CaMP2.

Once a mouse model has been crossed to also express an inducible GES, such as G-CaMP2 (MM-G-CaMP2), it may be used to study, e.g., calcium-involved events (and alterations to these events) including, but not limited to, calcium signaling, signal transduction, cell communication, and cell motility. Methods to study the MM-G-CaMP2 mouse model include those described herein and others known in the art. A skilled artisan will recognize that the methods used to study the MM-G-CaMP2 mouse model depend upon the disease, targeted tissue, and the intended use of the invention. For example, to study the development process, mice must be time-mated to allow embryos at different stages throughout development to be studied. Methods for studying mouse development are known in the art (see, Kaufman, M. H., 1999; and Rossant, J., 2002). Likewise, to study the aging process, mice must be allowed to age and analyzed at various stages during the aging process. Methods for studying mouse aging are known in the art (see, Hasty P. et al., 2003).

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd Ed. 1994); *The Cambridge Dictionary of Science and Technology* (Walker ed., 1988); The Glossary of Genetics, 5th Ed., R. Rieger et al. (eds.), Springer Verlag (1991); and Hale & Marham, *The Harper Collins Dictionary of Biology* (1991). As used herein, the following terms have the meanings ascribed to them.

A "fluorescent $Ca^{2+}$ indicator" or "FCIP" is a fusion protein based on the fusion of a fluorescent protein with a $Ca^{2+}$ sensitive protein. The binding of $Ca^{2+}$ to the $Ca^{2+}$ sensitive protein results in a conformational change of the fusion protein that in turn results in fluorescence. The $Ca^{2+}$ sensitivity of the fluorescence readout of FCIPs is generally achieved either via changes in the efficiency of fluorescence resonance energy transfer between two spectral variants of fluorescent proteins or via changes in the pKa of circularly permuted spectral variants of fluorescent proteins.

As used herein, a "transgenic mouse" is a mouse, in which one or more of the cells of the animal include a transgene.

A "transgene" is exogenous DNA that is integrated into the genome of a cell from which a transgenic animal develops and that remains in the genome of the mature animal, thereby directing the expression of an encoded gene product in one or more cell types or tissues of the transgenic animal.

"Subject", "organism", or "animal" as used herein means a living being having a central nervous system. Suitable subjects include: mammals, humans, mice, rats, dogs, cats, cattle, swine, sheep, and ungulates.

An "inducible system" refers to the components necessary to allow temporally controlled expression of a gene of interest. Typically, an inducible system includes an "inducible promoter" that is engineered to contain binding sites for specific substrates not present endogenously. For example, the tetracycline-based inducible system is based on regulatory elements from the Tn10-encoded tetracycline resistance operon from *E. coli* that can be regulated by tetracycline or derivatives of tetracycline. The tetracycline inducible system uses a tetracycline transactivator protein (tTA), tetracycline resistance operon nucleic acid sequences from *E. coli* (tetO), and tetracycline or a derivative thereof. In the absence of tetracycline, the tTA protein binds to tetO sequences placed upstream of a gene of interest to activate transcription. In the presence of tetracycline, the tTA protein is unable to bind to tetO sequences and transcription is prevented.

A "tetracycline transactivator" is a protein that has the ability to bind to tetracycline resistance operon (tetO) sequences to activate transcription and is tetracycline sensitive.

The term "tissue-specific regulatory element" means that a given polynucleotide sequence, e.g. a promoter, is transcriptionally active (i.e., directs, the expression of linked sequences sufficient to permit detection of the polypeptide product of the promoter) in less than all cells or tissues of an organism. A tissue-specific regulatory element, which may include a promoter, is preferably active in only one cell type, but may, for example, be active in a particular class or lineage of cell types (e.g., hematopoietic cells). A tissue-specific regulatory element useful according to the invention comprises those sequences necessary and sufficient for the expression of an operably linked nucleic acid sequence in a manner or pattern that is essentially the same as the manner or pattern of expression of the gene linked to that promoter in nature. As noted above, any tissue-specific transcriptional regulatory element known in the art may be used with the invention. Such regulatory elements may be used alone (i.e., a promoter only) or in combination with other regulatory elements.

The term "ubiquitous regulatory element" refers to any regulatory element, including a promoter, natural or engineered, that displays strong activity in a wide range of cells, tissues and cell cycles. Exemplary ubiquitous promoters include, but are not limited to, ubiquitinase, CMV, β-actin, GAPDH, β-kinesin, ROSA, and phosphoglycerate kinase promoters.

The term "operably linked" or "operatively linked" refers to the association of nucleic acid sequences on a single nucleic acid fragment so that the function of one is regulated by the other. For example, a regulatory element, such as a promoter, is operably linked with a coding sequence when it is capable of regulating the expression of that coding sequence (i.e., that the coding sequence is under the transcriptional control of the promoter). Coding sequences can be operably linked to regulatory elements in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA. Generally, operably linked means that the nucleic acid sequences being linked are contiguous and, where necessary to join two protein coding regions, contiguous and in the same reading frame.

The term "population of cells" refers to one or more cells arising from at least one stem cell. This includes intact tissue, fractionated/homogenized tissue, cells derived from a tissue, and stem cell cultures isolated from a tissue.

The term "expression", as used herein, refers to the production of a functional end product.

The term "module", as used herein, refers to a subject having within its genome one component, or construct, that is part of a multi-component, or construct, system. Herein, a module can be a transgenic animal, such as a "transgenic mouse" having at least one construct inserted into its genome. A "compound transgenic mouse" or "transgenic mouse model," which phrases may be used interchangeably herein as the context dictates, has at least two constructs inserted into its genome. For example, the tetracycline inducible system is a binary system that depends upon two constructs: one encoding a transactivator protein, and one encoding a gene of interest downstream of an inducible promoter containing tetO sequences. The two constructs, or modules, work together to produce inducible regulation of the expression of the gene of interest. Each module can be used interchangeably with other modules that provide either the transactivator protein targeted to one of many tissues, or one of many genes of interest.

The invention now being generally described, it will be more readily understood by reference to the following examples, which are included merely for purposes of illustration of certain aspects and embodiments of the present invention, and are not intended to limit the invention.

EXAMPLES

Example 1

In Vitro Mammalian Expression of G-CaMP2

Early versions of G-CaMP were not ideal for mammalian expression systems because they, inter alia, did not fold correctly at physiological temperatures. G-CaMP2, however, is thermally stable and retains brightness at 37° C. These properties of G-CaMP2 were analyzed in vitro using a mammalian expression system. To test the properties of G-CaMP2, human embryonic kidney cells (HEK 293) were transfected with a plasmid containing G-CaMP2 (pN1-G-CaMP2) and incubated at 37° C. for 48 hours. Cells expressing G-CaMP2 exhibited basal levels of fluorescence when excited at 488 nm. Acetylcholine was then used to activate G-protein coupled muscarinic acetylcholine receptors and mobilize intracellular calcium. After treatment with 10 µM acetylcholine, cells expressing G-CaMP2 exhibited an increase in fluorescence, thus allowing an increase in intracellular calcium to be visualized.

Example 2

TetO G-CaMP2 Construction

The properties of G-CaMP2 make it an ideal GES to use to monitor calcium fluctuations in vivo in multiple cell types. In order to increase the ease of using G-CaMP2 in multiple cell types, G-CaMP2 was combined with an inducible system with independent targeting potential. The tetracycline inducible system provides tissue-specific targeting separate from the gene of interest, so multiple cell types may be targeted by only changing one component of the system instead of both components.

The gene of interest component of the tetracycline inducible system was generated by placing the expression of the G-CaMP2 sensor under the control of the tetracycline promoter (TetO-G-CaMP2) using standard genetic engineering methods (FIG. 3B). The G-CaMP2 used by the invention includes a N-terminal HIS tag of 6 HIS residues (FIGS. 13A and 13B). The tetracycline promoter contains a minimal CMV promoter regulated by 4 tetO sequences (FIGS. 13A and 13B). Transcription of the resulting construct is active in the presence of tTA; therefore, the functionality of the construct was tested in the presence and absence of tTA in a mammalian expression system.

Human embryonic kidney cells (HEK 293) were co-transfected with TetO-G-CaMP2 and a construct containing a tetracycline transactivator protein under the control of a ubiquitous promoter (CMV-VP22-tTA). The cells were incubated at 37° C. for 48 hours and approximately 40% of the transfected cell population exhibited fluorescence when excited at 488 nm (FIG. 1A). When this population of cells was challenged with 10 µM acetylcholine to activate G-protein coupled muscarinic acetylcholine receptors to mobilize intracellular calcium, a subset of cells responded with a robust increase in fluorescence (FIG. 1B, arrows A, B, and C). The increase in fluorescence observed in cell A was approximately 90 AFU (FIG. 2A), cell B was approximately 95 AFU (FIG. 2B), and cell C had an increase of approximately 50 AFU (FIG. 2C). The change in fluorescence indicated proper function of the G-CaMP2 sensor combined with the tetracycline inducible system.

Example 3

Generation of TetO-G-CaMP2 Mouse

Figure 4F:
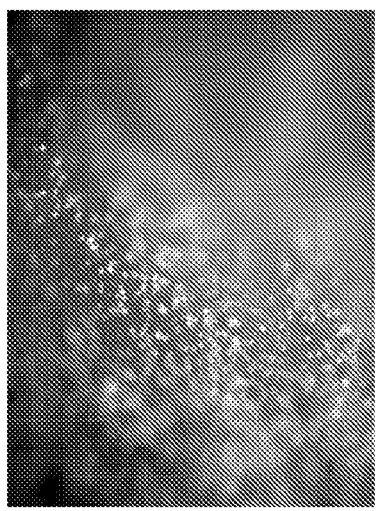
Figure 4B:
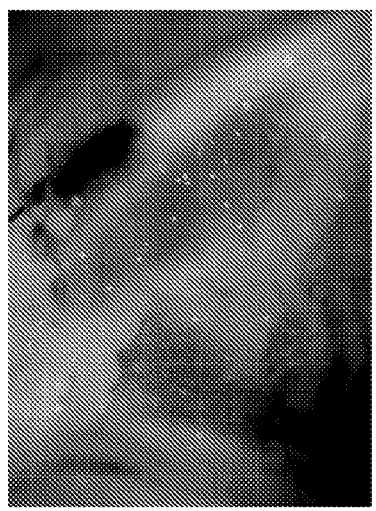
Figure 4E:
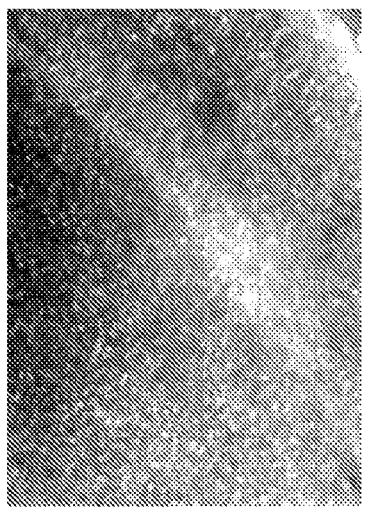
Figure 4A:
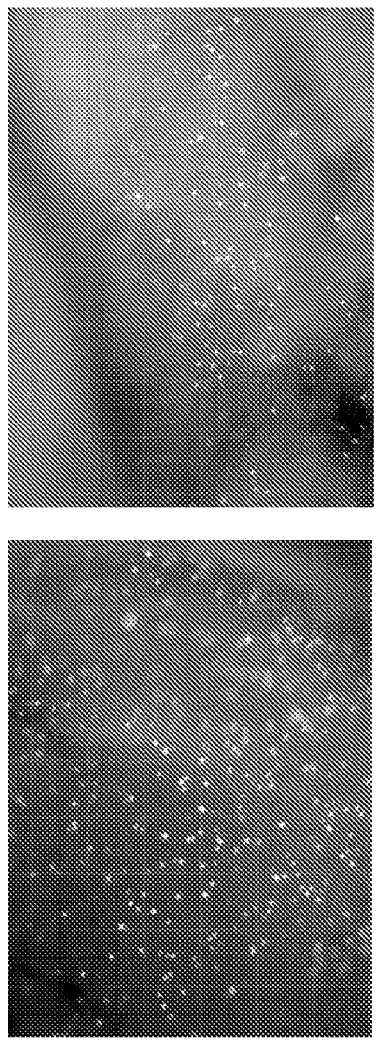
Figure 4D:
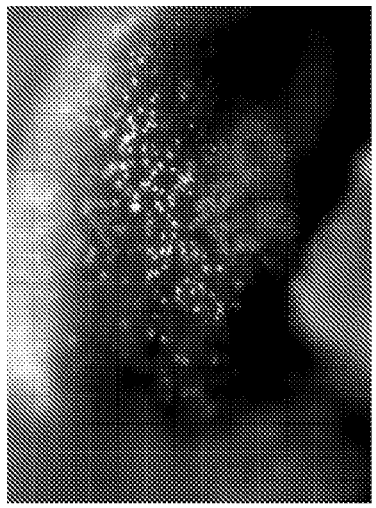
Figure 7B:
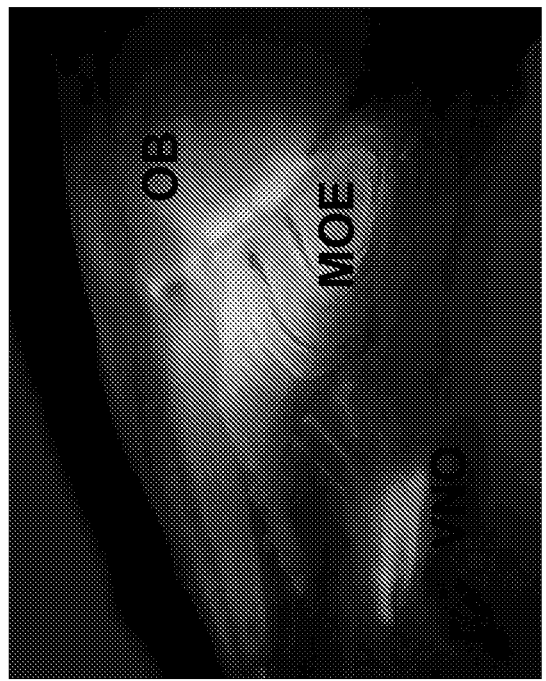
FIG. 7B demonstrates the targeting of G-CaMP2 to the olfactory bulb (OB), main olfactory epithelium (MOE), and vomeronasal organ (VNO).
Figure 7A:
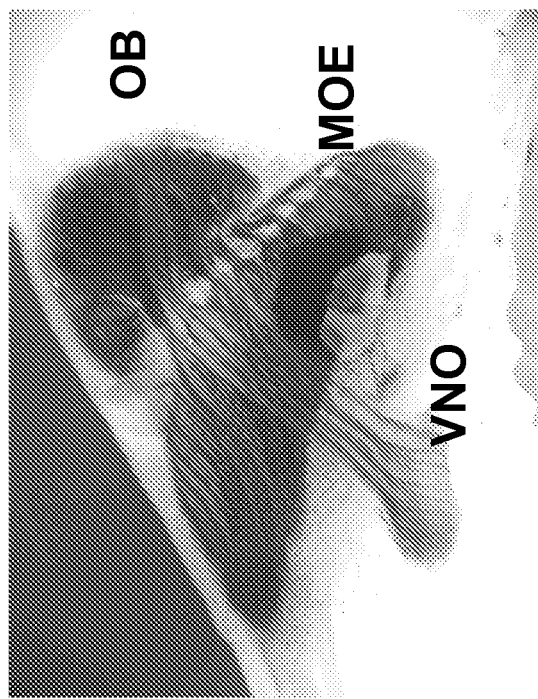
FIG. 7 shows the expression pattern targeted by the OMP promoter. A tissue sample isolated from a mouse expressing the marker tauLacZ gene from the OMP locus. This line marks all the sensory neurons in the olfactory system (FIG. 7A). The targeted expression of G-CaMP2 by the OMP promoter using the tetracycline multi-module system described herein (OMP-tTA-G-CaMP2) is shown to faithfully target G-CaMP2 according to the expression pattern of OMP.

A TetO-G-CaMP2 mouse was generated by linearizing the TetO-G-CaMP2 construct using restriction enzymes. The linearized construct was injected into the pronuclei of fertilized eggs placed in a surrogate mother. From three independent injections, 14 founder mice carrying the transgene were identified by PCR of tail extracted DNA. The 14 founder mice were crossed to a mouse from the OMP-IRES-tTA line (FIG. 3A), which expresses tTA from the OMP allele, targeting it to sensory neurons (FIGS. 7A and 7B). The levels of transgene expression were analyzed in compound offspring of the crosses by examining the number of cells that expressed G-CaMP2 in the olfactory epithelium or the vomeronasal organ. The intensity of fluorescence from individual cells was also assessed as an indicator of the level of expression. G-CaMP2 expression in founder Line 1 (FIG. 4A), Line 3 (FIG. 4B), Line 4 (FIG. 4C), Line 5 (FIG. 4E), Line 8 (FIG. 4D), and Line 10 (FIG. 4F) was at detectable levels with Lines 5 and 10 exhibiting the highest expression levels. The high expression levels allow expression to be detected at the gross level (FIG. 8A) and cellular level (FIGS. 8B and 8C). For example, fluorescence by Line 5 mice was visible through the skull to the naked eye.

Example 4

Monitoring Olfactory Neuron Stimulation

Figures 5A, 5B, 5C:
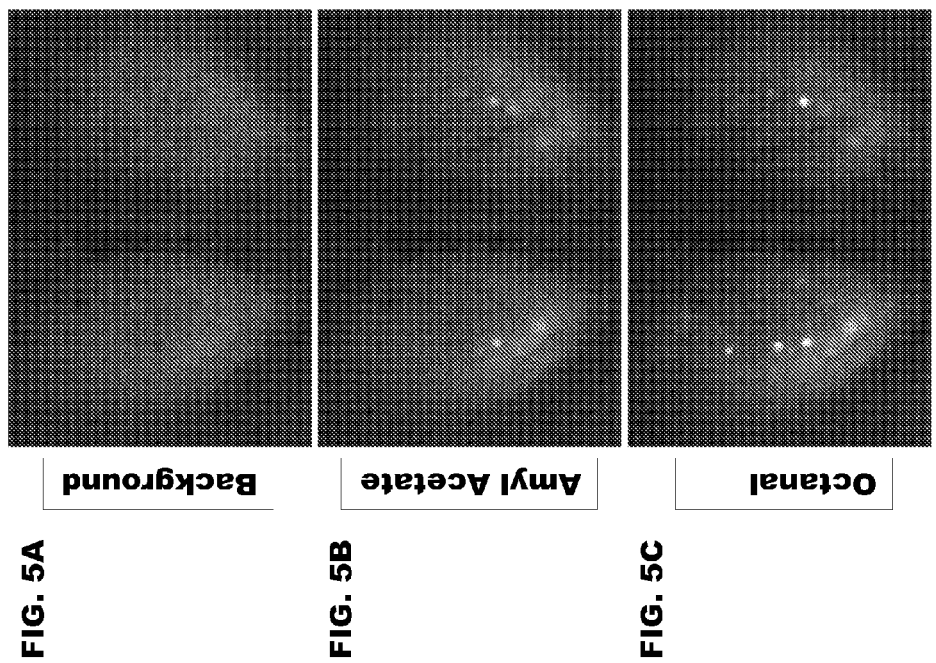
FIG. 5 shows the neuronal response to odor stimulation. The neuronal response of a line 5 OMP-tTA-G-CaMP2 compound transgenic mouse was imaged through the skull. Background fluorescence was detected before odor stimulation (FIG. 5A). The odor of amyl acetate, delivered to the nose of the mouse, resulted in activation of G-CaMP2 fluorescence in several glomeruli (FIG. 5B). The odor of octanal also resulted in activation of several glomeruli as shown by the G-CaMP2 fluorescence (FIG. 5C).
Figure 6:
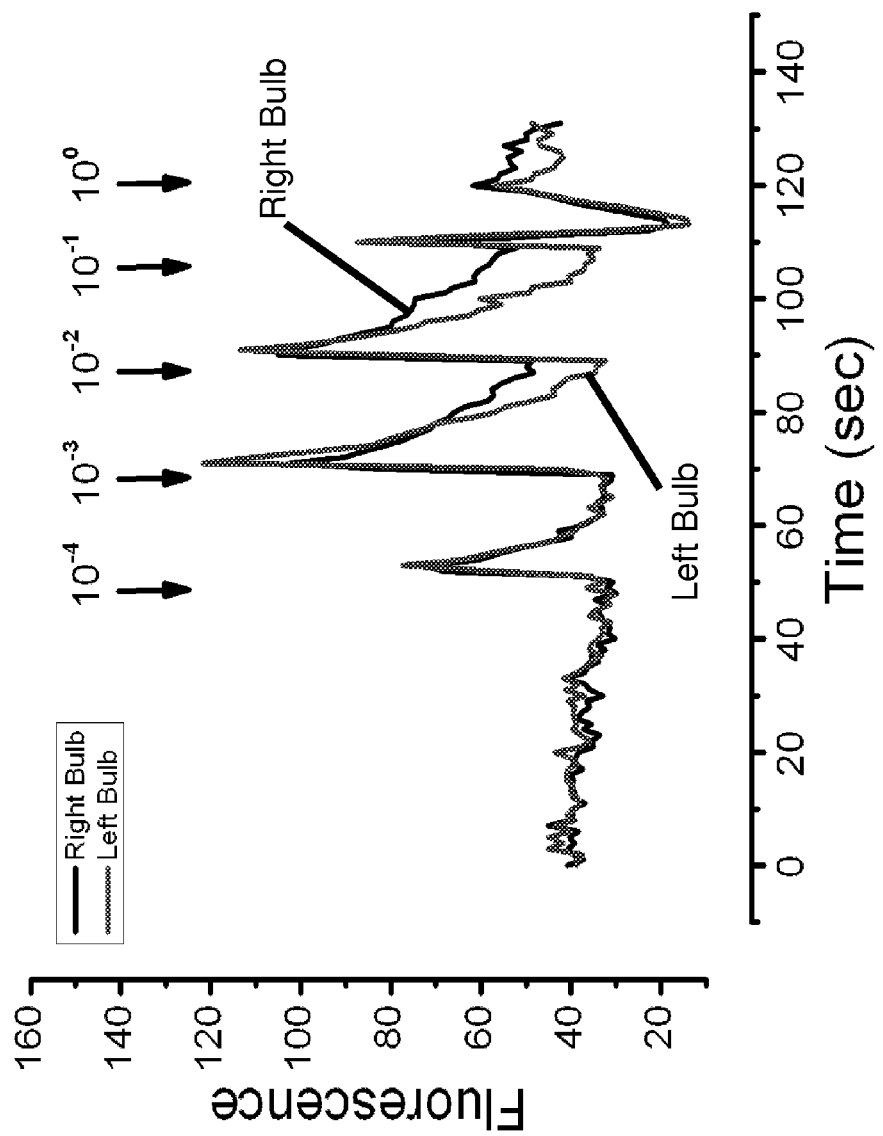
FIG. 6 is a graph that demonstrates the quantitative analysis of the response of a compound transgenic mouse to different concentrations of amyl acetate stimulation over time. An OMP-tTA-G-CaMP2 compound transgenic mouse from Line 5 was stimulated with different concentrations of amyl acetate and the resultant fluorescence was imaged through the skull. Both the right olfactory bulb and the left olfactory bulb were similarly stimulated.

The compound transgenic mice ("transgenic mice") containing the G-CaMP2 indicator targeted to the olfactory neurons may be used to evaluate neuron stimulation and map the signals sent in the brain. The response of sensory neurons was analyzed by stimulating transgenic mice with odor of varying concentrations. After anesthetizing mice with an injection of ketamine, the skin over the olfactory bulb was removed and the underlying skull covering the olfactory bulb was surgically thinned. The mice were then secured on an imaging plate and placed underneath a fluorescent microscope for imaging analysis. Background fluorescence was detected before odor stimulation (FIG. 5A). The odor of amyl acetate, delivered to the nose of the mouse, resulted in several glomeruli activating G-CaMP2 fluorescence (FIG. 5B). The odor of octanal also resulted in the response of several glomeruli to activate G-CaMP2 fluorescence (FIG. 5C). Amyl Acetate of various concentrations was also delivered to the nose of the animals using a custom made olfactometer. The resulting quantitative analysis of the response indicated that both the right and left olfactory bulbs were similarly stimulated (FIG. 6). Odor delivery excited the sensory neurons, which generated action potentials that reached both olfactory bulbs.

Figure 9C:
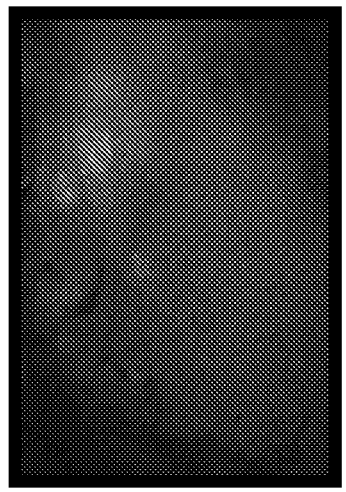

Different odors were found to activate different sensory neurons. OMP-tTA-G-CaMP2 mice were presented with three different odors that resulted in three different subsets of neurons becoming activated. Amyl acetate activated different neurons (FIGS. 9A and 12A) than those activated by butyraldehyde (FIGS. 9B and 12B) or hexanoic acid (FIG. 9C). When OMP-tTA-G-CaMP2 mice were presented with the combination of amyl acetate and butyraldehyde odors different glomeruli were activated (FIGS. 12C and 12D), than when either odor was presented alone (FIGS. 12A and 12B, respectively). The concentration of odor presented also activated glomeruli in a dose dependent manner (FIGS. 12C and 12D).

Figures 10A, 10B, 10C, 10D:
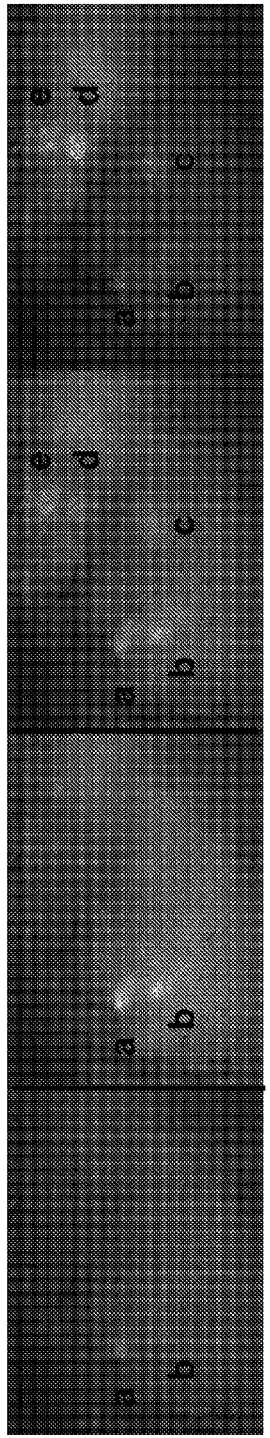
FIG. 10 shows the sequential activation of glomeruli of OMP-tTA-G-CaMP2 mice by the odor of octanal through the un-thinned skull. Initially, only two glomeruli are activated (FIGS. 10A and 10B). Over time, more glomeruli become activated as the initially activated glomeruli become less activated (FIGS. 10C and 10D). The fluorescence intensity of glomeruli a, b, c, d, and e fluctuates over the course of odor exposure (FIG. 10E).
Figure 10E:
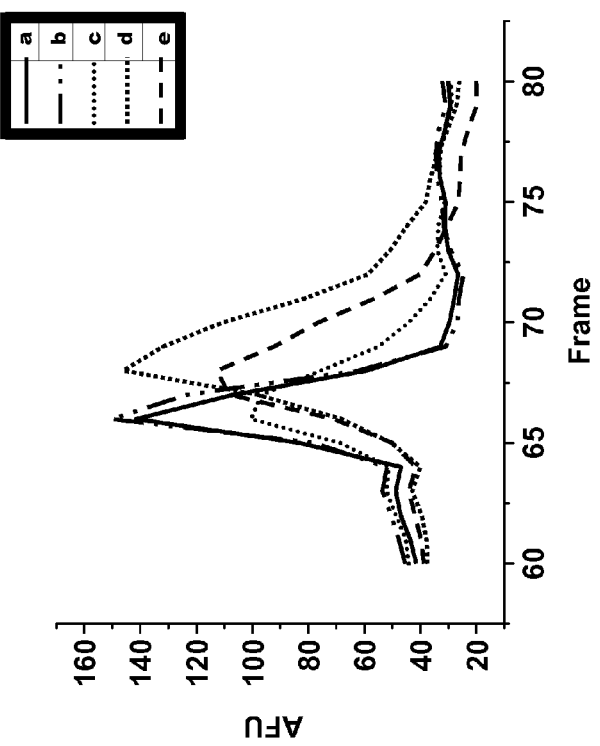

The length of odor exposure to different odors resulted in different expression profiles of neurons. The odor of octanal activated several different glomeruli sequentially (FIGS. 10A, 10B, 10C, and 10D) and as the sequence progressed, the neurons initially activated exhibited a decrease in G-CaMP2 expression (FIGS. 10C, 10D, and 10E). The odor of butyraldehyde also sequentially activated glomeruli (FIGS. 11A, 11B, 11C, and 11D). But, as the sequence progressed, the intensity of G-CaMP2 expression continued to increase (FIG. 11E).

Example 5

Live Animal Imaging Protocol

Animals are anesthetized with Ketamin/Xylazine cocktail and the righting reflex of the hind limbs are tested prior to surgery. Once deeply anesthetized, the hair over the head is shaved with a razor blade and a midline incision is made in the skin covering the skull to expose the olfactory bulb. For direct imaging, a head holder is glued to the bone and the animal is mounted to the microscope stage with the olfactory bulb region positioned right under the lens. (FIGS. 9 and 10). For bone thinning imaging, micro dental tools wet with saline are used to scrape the surface of the bone covering the olfactory bulb. Occasional air puffs are used to cool the thinning surface to prevent heat damage of the brain tissue. We normally stop when the bone can be indented by the gentle tough of a forceps tip, which is about 50 µm thick. The surface is then gently cleaned with saline and the head holder is attached for mounting the animal to the microscope.

Deposit

Tet-G2 transgenic embryos of the invention were deposited with the Patent Depository of the American Type Culture Collection, 10801 University Blvd., Manassas, Va. 20110-2209, USA (ATCC) on Oct. 23, 2007 and assigned Patent Deposit No. PTA-8714. These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Applicant and ATCC, which assures permanent and unrestricted availability of the deposit to the public upon issuance of the pertinent U.S. patent or upon laying open to the public of any U.S. or foreign patent application, whichever comes first, and assures availability of the deposit to one determined by the U.S. Commissioner of Patents and Trademarks to be entitled thereto according to 35 USC §122 and the Commissioner's rules pursuant thereto (including 37 CFR §1.14 with particular reference to 886 OG 638).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

CITED DOCUMENTS

The following documents, as well as those cited within this specification, are specifically incorporated by reference to the extent that they provide or teach exemplary methodology, techniques and/or compositions supplemental to those employed herein.

1. Baneriji et al., *Cell* 33:729-740, 1983
2. Berrettini, W. H., T. N. Ferraro, R. C. Alexander, A. M. Buchberg, and W. H. Vogel. 1994. Quantitative trait loci mapping of three loci controlling morphine preference using inbred mouse strains. *Nature Genet.* 7: 54-58.
3. Bullard, D. C., et al., *Am. J. Physiol. Gastrointest. Liver Physiol.* 283:G1232-G1237, December 2002
4. Byrne et al., *Proc. Natl. Acad. Sci. USA* 86:5473-5477, 1989
5. Calame et al., *Adv. Immunol.* 43:235-275, 1988
6. Campes et al., *Genes Dev.* 3:537-546, 1989
7. *Current Protocols in Molecular Biology*, Unit 1.5, pub, John Wiley & Sons, Inc., 1998.
8. Crabbe, J. C., J. K. Belknap, and K. J. Buck. 1994. Genetic animal models of alcohol and drug abuse. *Science* 264: 1715-1723.
9. De Sanctis, G. T., M. Merchant, D. R. Beier, R. D. Dredge, J. K. Grobholz, T. R. Martin, E. S. Lander, and J. M. Drazen. 1995. Quantitative locus analysis of airway hyper-responsiveness in A/J and C57BL/6J mice. *Nature Genet.* 11: 150-154.
10. Diez-Garcia, J., et al. *Eur. J. Neurosci.* 22:627-635, 2005
11. Edlunch et al., *Science* 230:912-916, 1985
12. Frankel, W. N., B. A. Taylor, J. L. Noebels, and C. M. Lutz. 1994. Genetic epilepsy model derived from common inbred mouse strains. *Genetics* 138: 481-489.
13. Fruh, K., et al. *EMBO J.* 13:3236-3244, 1994
14. Furth, P. A., et al. *PNAS* 91:9302-9306, 1994
15. Fussenegger M., *Biotechnol. Prog.* 17: 1-51, 2001
16. Go, W. Y. and Ho, S. N., *J. Gene Med.* 4: 258-270, 2002
17. Hasty, P., Campisi, J., Hoeljmakers, J., Van Steeg, H., and Vijg, J. Aging and genome maintenance: Lessons from the mouse?: Aging, *Science,* 299:1355-1359, 2003.
18. Hogan, In: MANIPULATING THE MOUSE EMBRYO, Cold Spring Harbor Laboratory Press, Cold Spring Harbor, and N.Y, 1986.
19. Hyman, R. W., S. Frank, C. H. Warden, A. Daluiski, R. Heller, and A. J. Lusis. 1994. Quantitative trait locus analysis of susceptibility to diet-induced atherosclerosis in recombinant inbred mice. *Biochem. Genet.* 32: 397-407.
20. Kaufman, M. H., and Bard, J. B. L. The Anatomical Basis of Mouse Development. Academic Press, San Diego, Calif. 1999.
21. Kellendonk C. et al. *Mol Biol* 285:175-182, 1999
22. Kessel et al., *Science* 249:374-379, 1990
23. Kistner, A., et al. *PNAS* 93:10933-10938, 1996
24. Kuhn R. et al. *Science* 269: 1427-1429, 1995
25. Metzger et al. *Eur. J. Neurosci.* 15:40-50, 2002
26. Pinkert et al., *Genes Dev.* 1:268-277, 1987
27. Queen and Baltimore, *Cell* 33:741-748, 1983
28. Rossant, J. and Tam, P. Mouse Development: Patterning, Morphogenesis, and Organogenesis, 2002.
29. Rubera I, et al. *J Am Soc Nephrol* 15: 2050-2056, 2004
30. Tallini, Y. N., et al. *PNAS* 103:4753-4758, 2006
31. U.S. Pat. No. 4,736,866, filed Jun. 22, 1984
32. U.S. Pat. No. 4,870,009 filed Dec. 15, 1983
33. U.S. Pat. No. 4,873,191, filed Aug. 18, 1986
34. U.S. Pat. No. 4,873,316, filed Jun. 23, 1987
35. West, D. B., J. Goudey-Lefevre, B. York, and G. E. Truett. 1994. Dietary obesity linked to genetic loci on chromosomes 9 and 15 in a polygenic mouse model. *J. Clin. Invest.* 94: 1410-1416.
36. Wimmel et al. *Oncogene* 9:995-997, 1994
37. Winoto et al., *EMBO J.* 8:729-733, 1989
38. Yun Bai, et al., *American journal of physiology. Renal physiology.* 52:F839-F851, 2002

What is claimed is:

1. A transgenic mouse comprising in its genome:
   (a) a first polynucleotide encoding a G-CaMP sensor linked to an inducible regulatory element comprising at least one tetracycline resistant operon (tetO) sequence; and
   (b) a second polynucleotide encoding a tetracycline transactivator operably linked to a tissue specific regulatory element comprising a tissue specific promoter, wherein the transgenic mouse expresses the G-CaMP sensor in a tissue specific manner and expression of the G-CaMP sensor is detectable in vivo.

2. The transgenic mouse according to claim 1, wherein the G-CaMP sensor is a G-CaMP2 sensor.

3. The transgenic mouse according to claim 1, wherein the tissue specific regulatory element is an olfactory marker protein (OMP) promoter.

4. A method for identifying a candidate compound that modulates intracellular calcium signaling comprising:
   (a) providing a candidate compound;
   (b) providing a transgenic mouse according to claim 1;
   (c) inducing expression of the G-CaMP sensor in the brain of the transgenic mouse
   (d) administering the candidate compound to the transgenic mouse; and
   (e) evaluating an effect, if any, of the candidate compound on intracellular calcium signaling in the transgenic mouse by detecting an alteration in fluorescence intensity of the G-CaMP sensor.

5. The method according to claim 4, wherein the evaluating step is performed non-invasively through a tissue of the mouse.

6. A method for identifying a candidate compound that modulates intracellular calcium signaling in the brain comprising:
   (a) providing a candidate compound;
   (b) providing a transgenic mouse comprising in its genome:
      (i) a first polynucleotide encoding a G-CaMP sensor linked to an inducible regulatory element comprising at least one tetO sequence and
      (ii) a second polynucleotide encoding a tetracycline transactivator operably linked to a brain-specific regulatory element comprising a brain-specific promoter;
   (c) inducing expression of the G-CaMP sensor in the brain;
   (d) administering the candidate compound to the brain of the transgenic mouse; and
   (e) evaluating an effect, if any, of the candidate compound on brain intracellular calcium signaling in the transgenic mouse by detecting an alteration in fluorescence intensity of the G-CaMP sensor in the brain.

7. The method according to claim 6, wherein the evaluating step is performed non-invasively through the skull of the mouse.

8. The method according to claim 6, wherein the evaluating step comprises thinning at least a portion of the mouse skull covering an area of interest.

9. The method according to claim 8, wherein the thinning comprises shaving the bone down to about 50 micron thickness.

10. The method according to claim 6, wherein the candidate compound is administered to the mouse through olfaction.

11. A method for identifying a candidate compound that modulates intracellular calcium signaling in the brain comprising:
   (a) providing a candidate compound;
   (b) providing a brain slice from a transgenic mouse comprising in its genome:
      (i) a first polynucleotide encoding a G-CaMP sensor linked to an inducible regulatory element comprising at least one tetO sequence and
      (ii) a second polynucleotide encoding a tetracycline transactivator operably linked to a brain-specific regulatory element comprising a brain-specific promoter,
   wherein the transgenic mouse expresses the G-CaMP sensor in the brain;
   (c) administering the candidate compound to the brain slice of the transgenic mouse; and
   (d) evaluating an effect, if any, of the candidate compound on brain intracellular calcium signaling in the transgenic mouse by detecting an alteration in fluorescence intensity of the G-CaMP sensor in the brain slice.

* * * * *

```
SEQUENCE LISTING

<160> NUMBER OF SEQ ID NOS: 2

<210> SEQ ID NO 1
<211> LENGTH: 2419
<212> TYPE: DNA
<213> ORGANISM: Aequorea victoria
<220> FEATURE:
<221> NAME/KEY: CDS
<222> LOCATION: (818)..(2170)

<400> SEQUENCE: 1
tagttattac tagcgctacc ggactcagat ctcgagttta ccactcccta tcagtgatag      60
agaaaagtga aagtcgagtt taccactccc tatcagtgat agagaaaagt gaaagtcgag     120
tttaccactc cctatcagtg atagagaaaa gtgaaagtcg agtttaccac tccctatcag     180
tgatagagaa aagtgaaagt cgagtttacc actccctatc agtgatagag aaaagtgaaa     240
gtcgagttta ccactcccta tcagtgatag agaaaagtga aagtcgagtt taccactccc     300
tatcagtgat agagaaaagt gaaagtcgag ctcggtaccc gggtcgaggt aggcgtgtac     360
ggtgggaggc ctatataagc agagctcgtt tagtgaaccg tcagatcgcc tggagacgcc     420
atccacgctg ttttgacctc catagaagac accgggacc gatccagcct ccgcggcccc      480
```

```
gaattcacca cgtggccgca tcgattctag aattcgctgt ctgcgagggc cagctgttgg      540
ggtgagtact ccctctcaaa agcgggcatg acttctgcgc taagattgtc agtttccaaa      600
aacgaggagg atttgatatt cacctggccc gcggtgatgc ctttgagggt ggccgcgtcc      660
atctggtcag aaaagacaat cttttttgttg tcaagcttga ggtgtggcag gcttgagatc     720
tggccataca cttgagtgac aatgacatcc actttgcctt tctctccaca ggtgtccact      780
cccaggtcca actgcagccc aagcggatct cgccacc atg cgg ggt tct cat cat      835
                                      Met Arg Gly Ser His His
                                      1               5
```

| cat | cat | cat | cat | ggt | atg | gct | agc | atg | act | ggt | gga | cag | caa | atg | ggt | 883 |
|---|---|---|---|---|---|---|---|---|---|---|---|---|---|---|---|---|
| His | His | His | His | Gly | Met | Ala | Ser | Met | Thr | Gly | Gly | Gln | Gln | Met | Gly | |
| | | 10 | | | | 15 | | | | | 20 | | | | | |

| cgg | gat | ctg | tac | gac | gat | gac | aag | gat | ctc | gcc | acc | atg | gtc | gac | 931 |
|---|---|---|---|---|---|---|---|---|---|---|---|---|---|---|---|
| Arg | Asp | Leu | Tyr | Asp | Asp | Asp | Lys | Asp | Leu | Ala | Thr | Met | Val | Asp | |
| | | 25 | | | | 30 | | | | 35 | | | | | |

| tca | tca | cgt | cgt | aag | tgg | aat | aag | aca | ggt | cac | gca | gtc | aga | gct | ata | 979 |
|---|---|---|---|---|---|---|---|---|---|---|---|---|---|---|---|---|
| Ser | Ser | Arg | Arg | Lys | Trp | Asn | Lys | Thr | Gly | His | Ala | Val | Arg | Ala | Ile | |
| | 40 | | | | 45 | | | | | 50 | | | | | | |

| ggt | cgg | ctg | agc | tca | ctc | gag | aac | gtc | tat | atc | atg | gcc | gac | aag | cag | 1027 |
|---|---|---|---|---|---|---|---|---|---|---|---|---|---|---|---|---|
| Gly | Arg | Leu | Ser | Ser | Leu | Glu | Asn | Val | Tyr | Ile | Met | Ala | Asp | Lys | Gln | |
| 55 | | | | 60 | | | | | 65 | | | | | 70 | | |

| aag | aac | ggc | atc | aag | gcg | aac | ttc | aag | atc | cgc | cac | aac | atc | gag | gac | 1075 |
|---|---|---|---|---|---|---|---|---|---|---|---|---|---|---|---|---|
| Lys | Asn | Gly | Ile | Lys | Ala | Asn | Phe | Lys | Ile | Arg | His | Asn | Ile | Glu | Asp | |
| | | | 75 | | | | | 80 | | | | | 85 | | | |

| ggc | ggc | gtg | cag | ctc | gcc | tac | cac | tac | cag | cag | aac | acc | ccc | atc | ggc | 1123 |
|---|---|---|---|---|---|---|---|---|---|---|---|---|---|---|---|---|
| Gly | Gly | Val | Gln | Leu | Ala | Tyr | His | Tyr | Gln | Gln | Asn | Thr | Pro | Ile | Gly | |
| | | | 90 | | | | 95 | | | | | 100 | | | | |

| gac | ggc | ccc | gtg | ctg | ctg | ccc | gac | aac | cac | tac | ctg | agc | acc | cag | tcc | 1171 |
|---|---|---|---|---|---|---|---|---|---|---|---|---|---|---|---|---|
| Asp | Gly | Pro | Val | Leu | Leu | Pro | Asp | Asn | His | Tyr | Leu | Ser | Thr | Gln | Ser | |
| | 105 | | | | | 110 | | | | | 115 | | | | | |

| aaa | ctt | tcg | aaa | gac | ccc | aac | gag | aag | cgc | gat | cac | atg | gtc | ctg | ctg | 1219 |
|---|---|---|---|---|---|---|---|---|---|---|---|---|---|---|---|---|
| Lys | Leu | Ser | Lys | Asp | Pro | Asn | Glu | Lys | Arg | Asp | His | Met | Val | Leu | Leu | |
| | | 120 | | | | | 125 | | | | | 130 | | | | |

| gag | ttc | gtg | acc | gcc | gcc | ggg | atc | act | ctc | ggc | atg | gac | gag | ctg | tac | 1267 |
|---|---|---|---|---|---|---|---|---|---|---|---|---|---|---|---|---|
| Glu | Phe | Val | Thr | Ala | Ala | Gly | Ile | Thr | Leu | Gly | Met | Asp | Glu | Leu | Tyr | |
| 135 | | | | | 140 | | | | | 145 | | | | | 150 | |

| aag | ggc | ggt | acc | gga | ggg | agc | atg | gtg | agc | aag | ggc | gag | gag | ctg | ttc | 1315 |
|---|---|---|---|---|---|---|---|---|---|---|---|---|---|---|---|---|
| Lys | Gly | Gly | Thr | Gly | Gly | Ser | Met | Val | Ser | Lys | Gly | Glu | Glu | Leu | Phe | |
| | | | | 155 | | | | | 160 | | | | | 165 | | |

| acc | ggg | gtg | gtg | ccc | atc | ctg | gtc | gag | ctg | gac | ggc | gac | gta | aac | ggc | 1363 |
|---|---|---|---|---|---|---|---|---|---|---|---|---|---|---|---|---|
| Thr | Gly | Val | Val | Pro | Ile | Leu | Val | Glu | Leu | Asp | Gly | Asp | Val | Asn | Gly | |
| | | | 170 | | | | | 175 | | | | | 180 | | | |

| cac | aag | ttc | agc | gtg | tcc | ggc | gag | ggt | gag | ggc | gat | gcc | acc | tac | ggc | 1411 |
|---|---|---|---|---|---|---|---|---|---|---|---|---|---|---|---|---|
| His | Lys | Phe | Ser | Val | Ser | Gly | Glu | Gly | Glu | Gly | Asp | Ala | Thr | Tyr | Gly | |
| | | 185 | | | | | 190 | | | | | 195 | | | | |

| aag | ctg | acc | ctg | aag | ttc | atc | tgc | acc | acc | ggc | aag | ctg | ccc | gtg | ccc | 1459 |
|---|---|---|---|---|---|---|---|---|---|---|---|---|---|---|---|---|
| Lys | Leu | Thr | Leu | Lys | Phe | Ile | Cys | Thr | Thr | Gly | Lys | Leu | Pro | Val | Pro | |
| | 200 | | | | | 205 | | | | | 210 | | | | | |

| tgg | ccc | acc | ctc | gtg | acc | acc | ctg | acc | tac | ggc | gtg | cag | tgc | ttc | agc | 1507 |
|---|---|---|---|---|---|---|---|---|---|---|---|---|---|---|---|---|
| Trp | Pro | Thr | Leu | Val | Thr | Thr | Leu | Thr | Tyr | Gly | Val | Gln | Cys | Phe | Ser | |
| 215 | | | | | 220 | | | | | 225 | | | | | 230 | |

| cgc | tac | ccc | gac | cac | atg | aag | cag | cac | gac | ttc | ttc | aag | tcc | gcc | atg | 1555 |
|---|---|---|---|---|---|---|---|---|---|---|---|---|---|---|---|---|
| Arg | Tyr | Pro | Asp | His | Met | Lys | Gln | His | Asp | Phe | Phe | Lys | Ser | Ala | Met | |
| | | | | 235 | | | | | 240 | | | | | 245 | | |

| ccc | gaa | ggc | tac | atc | cag | gag | cgc | acc | atc | ttc | ttc | aag | gac | gac | ggc | 1603 |
|---|---|---|---|---|---|---|---|---|---|---|---|---|---|---|---|---|
| Pro | Glu | Gly | Tyr | Ile | Gln | Glu | Arg | Thr | Ile | Phe | Phe | Lys | Asp | Asp | Gly | |
| | | | | 250 | | | | | 255 | | | | | 260 | | |

| aac | tac | aag | acc | cgc | gcc | gag | gtg | aag | ttc | gag | ggc | gac | acc | ctg | gtg | 1651 |
|---|---|---|---|---|---|---|---|---|---|---|---|---|---|---|---|---|

```
                                                                                1699
aac cgc atc gag ctg aag ggc atc gac ttc aag gag gac ggc aac atc
Asn Arg Ile Glu Leu Lys Gly Ile Asp Phe Lys Glu Asp Gly Asn Ile
    280                 285                 290

1747
ctg ggg cac aag ctg gag tac aac acg cgt gac caa ctg act gaa gag
Leu Gly His Lys Leu Glu Tyr Asn Thr Arg Asp Gln Leu Thr Glu Glu
295                 300                 305                 310

1795
cag atc gca gaa ttt aaa gag gct ttc tcc cta ttt gac aag gac ggg
Gln Ile Ala Glu Phe Lys Glu Ala Phe Ser Leu Phe Asp Lys Asp Gly
                315                 320                 325

1843
gat ggg aca ata aca acc aag gag ctg ggg acg gtg atg cgg tct ctg
Asp Gly Thr Ile Thr Thr Lys Glu Leu Gly Thr Val Met Arg Ser Leu
330                 335                 340

1891
ggg cag aac ccc aca gaa gca gag ctg cag gac atg atc aat gaa gta
Gly Gln Asn Pro Thr Glu Ala Glu Leu Gln Asp Met Ile Asn Glu Val
        345                 350                 355

1939
gat gcc gac ggt aat ggc aca atc gac ttc cct gag ttc ctg aca atg
Asp Ala Asp Gly Asn Gly Thr Ile Asp Phe Pro Glu Phe Leu Thr Met
    360                 365                 370

1987
atg gca aga aaa atg aaa gac aca gac agt gaa gaa gaa att aga gaa
Met Ala Arg Lys Met Lys Asp Thr Asp Ser Glu Glu Glu Ile Arg Glu
375                 380                 385                 390

2035
gcg ttc cgt gtg ttt gat aag gat ggc aat ggc tac atc agt gca gca
Ala Phe Arg Val Phe Asp Lys Asp Gly Asn Gly Tyr Ile Ser Ala Ala
                395                 400                 405

2083
gag ctt cgc cac gtg atg aca aac ctt gga gag aag tta aca gat gaa
Glu Leu Arg His Val Met Thr Asn Leu Gly Glu Lys Leu Thr Asp Glu
            410                 415                 420

2131
gag gtt gat gaa atg atc agg gaa gca gac atc gat ggg gat ggt cag
Glu Val Asp Glu Met Ile Arg Glu Ala Asp Ile Asp Gly Asp Gly Gln
                425                 430                 435

2180
gta aac tac gaa gag ttt gta caa atg atg aca gcg aag tgagcggccg
Val Asn Tyr Glu Glu Phe Val Gln Met Met Thr Ala Lys
        440                 445                 450 cgactctaga tcataatcag ccataccaca tttgtagagg ttttacttgc tttaaaaaac    2240
ctcccacacc tcccccctgaa cctgaaacat aaaatgaatg caattgttgt tgttaacttg   2300
tttattgcag cttataatgg ttacaaataa agcaatagca tcacaaattt cacaaataaa   2360
gcattttttt cactgcattc tagttgtggt ttgtccaaac tcatcaatgt atcttaagg    2419
```

<210> SEQ ID NO 2
<211> LENGTH: 451
<212> TYPE: PRT
<213> ORGANISM: Aequorea victoria

<400> SEQUENCE: 2

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Leu Ala Thr Met Val Asp Ser Ser Arg Arg Lys Trp Asn Lys Thr Gly
        35                  40                  45

His Ala Val Arg Ala Ile Gly Arg Leu Ser Ser Leu Glu Asn Val Tyr
    50                  55                  60

Ile Met Ala Asp Lys Gln Lys Asn Gly Ile Lys Ala Asn Phe Lys Ile
65                  70                  75                  80

Arg His Asn Ile Glu Asp Gly Gly Val Gln Leu Ala Tyr His Tyr Gln
```

```
            85                  90                  95
Gln Asn Thr Pro Ile Gly Asp Gly Pro Val Leu Leu Pro Asp Asn His
            100                 105                 110

Tyr Leu Ser Thr Gln Ser Lys Leu Ser Lys Asp Pro Asn Glu Lys Arg
            115                 120                 125

Asp His Met Val Leu Leu Glu Phe Val Thr Ala Ala Gly Ile Thr Leu
            130                 135                 140

Gly Met Asp Glu Leu Tyr Lys Gly Gly Thr Gly Gly Ser Met Val Ser
145                 150                 155                 160

Lys Gly Glu Glu Leu Phe Thr Gly Val Val Pro Ile Leu Val Glu Leu
            165                 170                 175

Asp Gly Asp Val Asn Gly His Lys Phe Ser Val Ser Gly Glu Gly Glu
            180                 185                 190

Gly Asp Ala Thr Tyr Gly Lys Leu Thr Leu Lys Phe Ile Cys Thr Thr
            195                 200                 205

Gly Lys Leu Pro Val Pro Trp Pro Thr Leu Val Thr Thr Leu Thr Tyr
            210                 215                 220

Gly Val Gln Cys Phe Ser Arg Tyr Pro Asp His Met Lys Gln His Asp
225                 230                 235                 240

Phe Phe Lys Ser Ala Met Pro Glu Gly Tyr Ile Gln Glu Arg Thr Ile
            245                 250                 255

Phe Phe Lys Asp Asp Gly Asn Tyr Lys Thr Arg Ala Glu Val Lys Phe
            260                 265                 270

Glu Gly Asp Thr Leu Val Asn Arg Ile Glu Leu Lys Gly Ile Asp Phe
            275                 280                 285

Lys Glu Asp Gly Asn Ile Leu Gly His Lys Leu Glu Tyr Asn Thr Arg
            290                 295                 300

Asp Gln Leu Thr Glu Glu Gln Ile Ala Glu Phe Lys Glu Ala Phe Ser
305                 310                 315                 320

Leu Phe Asp Lys Asp Gly Asp Gly Thr Ile Thr Thr Lys Glu Leu Gly
            325                 330                 335

Thr Val Met Arg Ser Leu Gly Gln Asn Pro Thr Glu Ala Glu Leu Gln
            340                 345                 350

Asp Met Ile Asn Glu Val Asp Ala Asp Gly Asn Gly Thr Ile Asp Phe
            355                 360                 365

Pro Glu Phe Leu Thr Met Met Ala Arg Lys Met Lys Asp Thr Asp Ser
            370                 375                 380

Glu Glu Glu Ile Arg Glu Ala Phe Arg Val Phe Asp Lys Asp Gly Asn
385                 390                 395                 400

Gly Tyr Ile Ser Ala Ala Glu Leu Arg His Val Met Thr Asn Leu Gly
            405                 410                 415

Glu Lys Leu Thr Asp Glu Glu Val Asp Glu Met Ile Arg Glu Ala Asp
            420                 425                 430

Ile Asp Gly Asp Gly Gln Val Asn Tyr Glu Glu Phe Val Gln Met Met
            435                 440                 445

Thr Ala Lys
    450
```